United States Patent
Chung et al.

(10) Patent No.: US 10,689,426 B2
(45) Date of Patent: Jun. 23, 2020

(54) ARTIFICIAL SYNAPSE INDUCER AND METHOD OF MAKING THE SAME

(71) Applicant: SEOUL NATIONAL UNIVERSITY R&DB FOUNDATION, Seoul (KR)

(72) Inventors: Taek Dong Chung, Gwacheon-si (KR); In Seong Hwang, Seoul (KR); Eun Joong Kim, Yongin-si (KR); Chang Su Jeon, Yeosu-si (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 16/155,209

(22) Filed: Oct. 9, 2018

(65) Prior Publication Data

US 2019/0119343 A1 Apr. 25, 2019

Related U.S. Application Data

(63) Continuation of application No. 14/786,908, filed as application No. PCT/KR2013/007423 on Aug. 19, 2013, now abandoned.

(30) Foreign Application Priority Data

Apr. 24, 2013 (KR) ........................ 10-2013-0045763

(51) Int. Cl.
  *C07K 14/475* (2006.01)
  *C07K 14/705* (2006.01)
  *C07K 14/435* (2006.01)
  *C12N 5/0793* (2010.01)

(52) U.S. Cl.
  CPC .... *C07K 14/4756* (2013.01); *C07K 14/43595* (2013.01); *C07K 14/705* (2013.01); *C12N 5/0619* (2013.01); *C07K 2319/20* (2013.01); *C07K 2319/21* (2013.01); *C07K 2319/40* (2013.01); *C07K 2319/42* (2013.01); *C07K 2319/60* (2013.01); *C07K 2319/90* (2013.01); *C12N 2501/13* (2013.01); *C12N 2501/58* (2013.01); *C12N 2533/50* (2013.01)

(58) Field of Classification Search
  CPC ........................ C07K 14/4756; C07K 2319/33
  See application file for complete search history.

(56) References Cited

PUBLICATIONS

Baksh et al., "Neuronal Activation by GPI-Linked Neuroligin-1 Displayed in Synthetic Lipid Bilayer Membranes", Langmuir, vol. 21, No. 23—13 pages (Nov. 8, 2005).

Chen, "Site-specific Labeling of Cellular Proteins with Unnatural Substrates of Biotin Ligase", Stanford University—308 pages (Sep. 2007).

Dean et al., "Neurexin mediates the assembly of presynaptic terminals", Nature Neuroscience, vol. 6, No. 7—19 pages (Jul. 2003).

Gerrow et al., "Trafficking of scaffolding and adhesion proteins: The role of pre-assembled complexes and lateral diffusion during synapse development", University of British Columbia—208 pages (Oct. 2008).

Howarth et al., "A monovalent streptavidin with a single femtomolar biotin binding site", Nat. Methods, vol. 3, No. 4—15 pages (Apr. 2006).

International Search Report of PCT/KR2013/007423 which is the parent application and its English translation—6 pages (dated Jan. 23, 2014).

Kim et al., "Patterning Artificially Induced Synapses for Neural Interfaces", 63rd Annual Meeting of the International Society of Electrochemistry—4 pages (Aug. 2012).

Pautot et al., "Neuronal synapse interaction reconstituted between live cells and supported lipid bilayers", Nat. Chem. Biol., vol. 1, No. 5—14 pages (Oct. 2005).

Peixoto et al., "Trans-Synaptic Signaling by Activity-Dependent Cleavage of Neuroligin-1," Neuron vol. 76, No. 2—29 pages (Oct. 18, 2012).

Scheiffele et al., "Neuroligin Expressed in Nonneuronal Cells Triggers Presynaptic Development in Contacting Axons", Cell, vol. 101, No. 6—13 pages (Jun. 9, 2000).

*Primary Examiner* — Robert C Hayes
(74) *Attorney, Agent, or Firm* — Knobbe Martens Olson & Bear LLP

(57) ABSTRACT

Disclosed is a polypeptide containing an extracellular domain of a synaptogenic protein, and a method for manufacturing a nerve cell, a complex containing a biotin tagged at the C-terminus of the polypeptide, an artificial synapse inducer for coupling the composite to a streptavidin (SAV)-coated substrate and a nerve cell. The complex tagged with a biotin at the C-terminus of the polypeptide containing the extracellular domain of the synaptogenic protein, such as neuroligin-1, can display activity by being attached to the SAV-coated substrate to adjust the orientation thereof without help of a supported lipid bilayer. The complex containing an additional RFP between the extracellular domain and the biotin of the synaptogenic protein not only facilitates easier mass-production, quantification, and tracking, but also displays activity of a normal synaptogenic protein, thereby inducing excitatory or inhibitory synaptic differentiation by being fixed to the substrate and added to the nerve cell culture.

14 Claims, 15 Drawing Sheets
Specification includes a Sequence Listing.

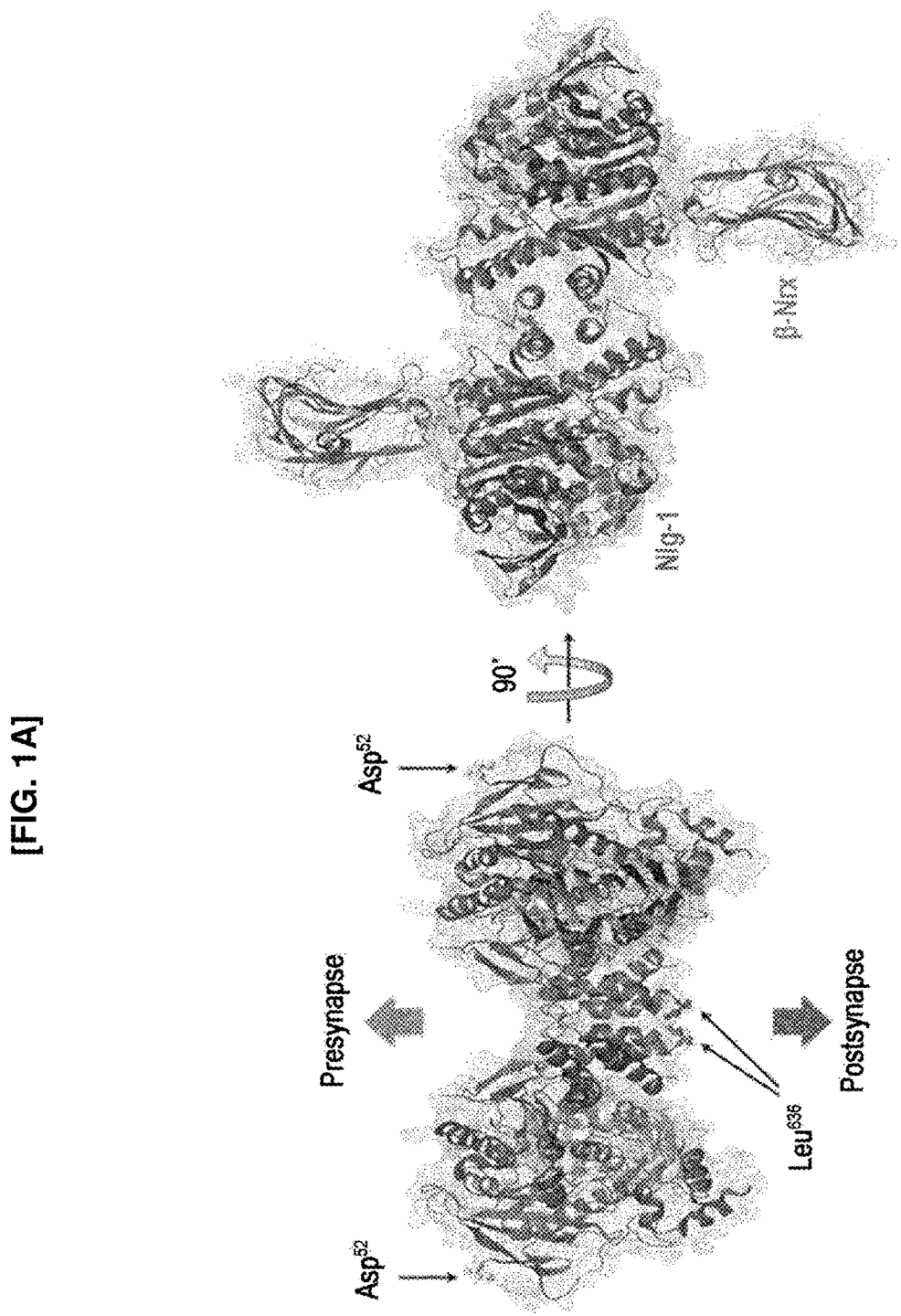
[FIG. 1A]

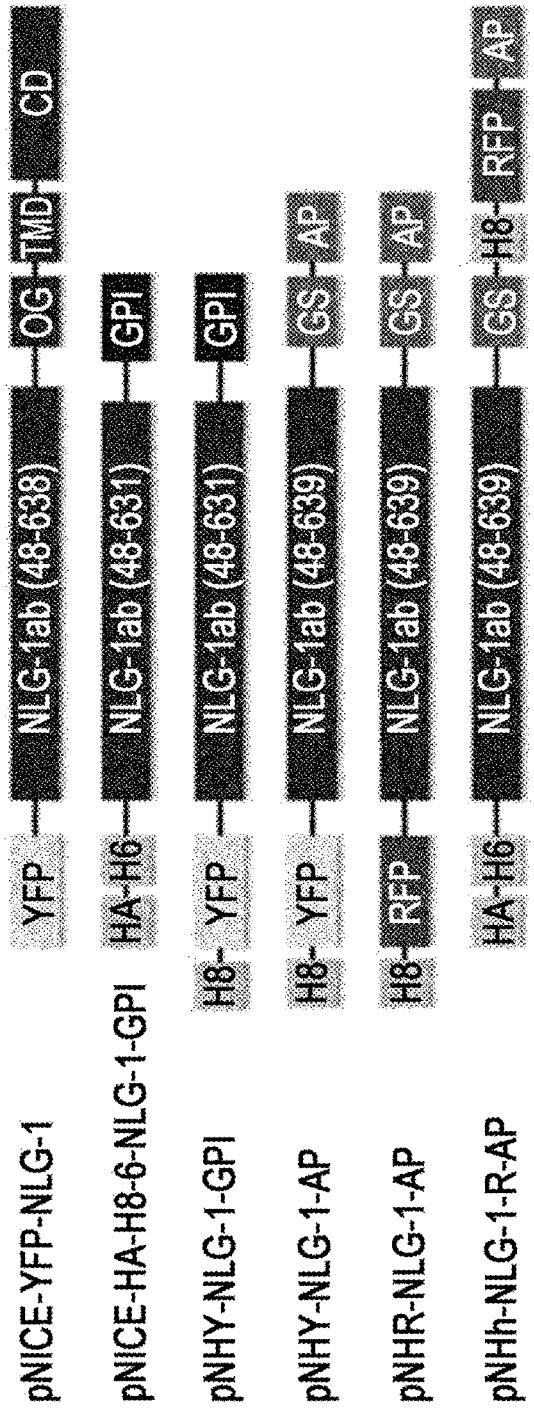
[FIG. 1B]

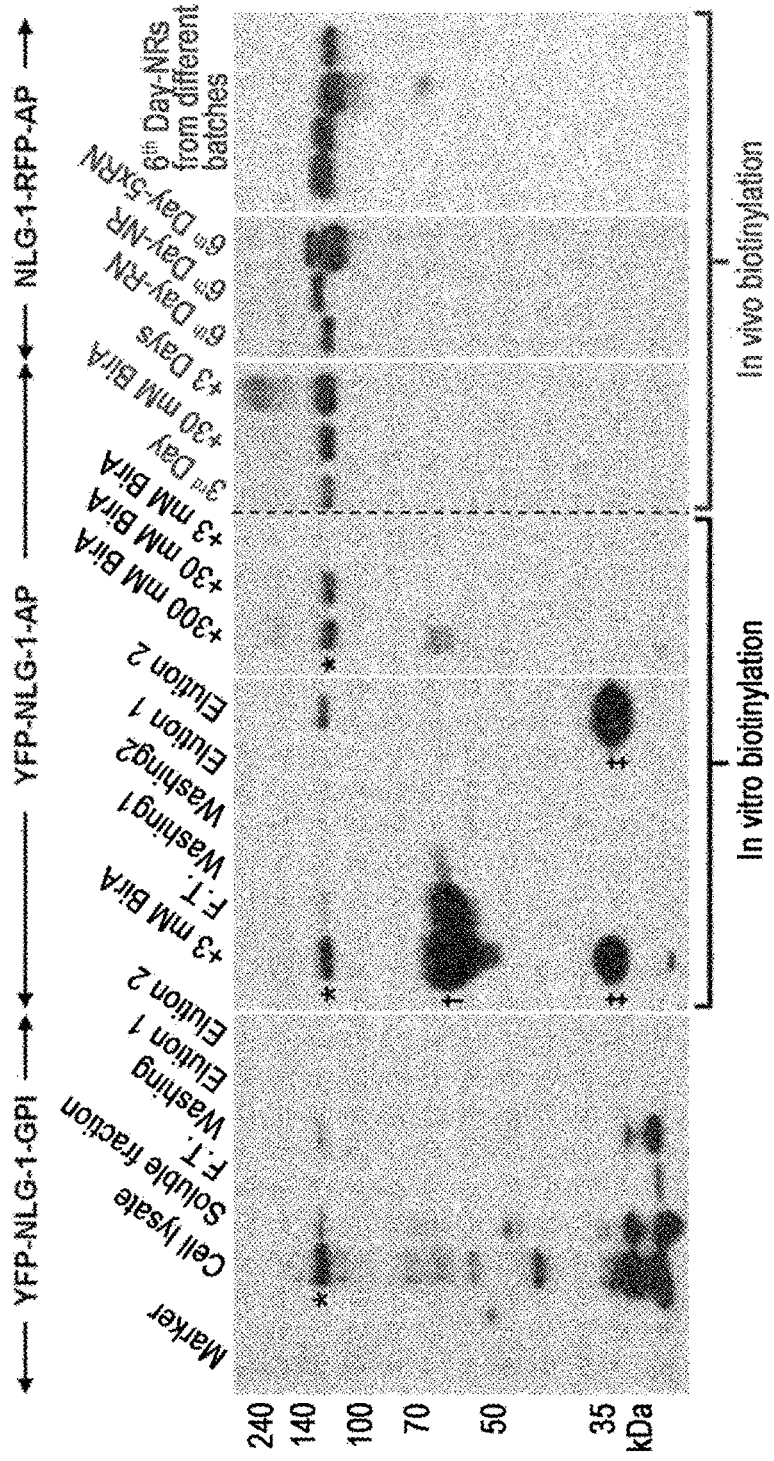
[FIG. 2]

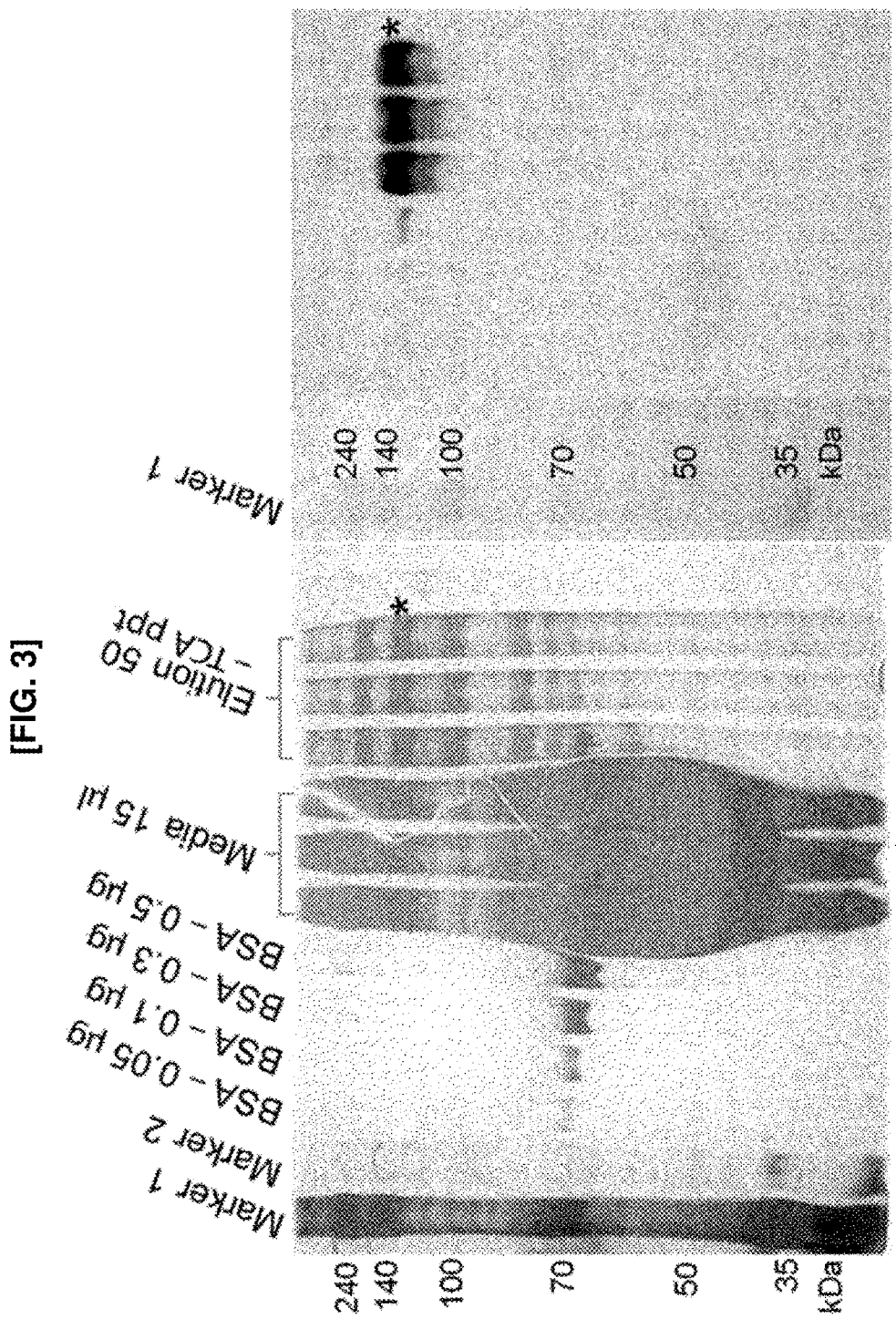
[FIG. 3]

[FIG. 4]
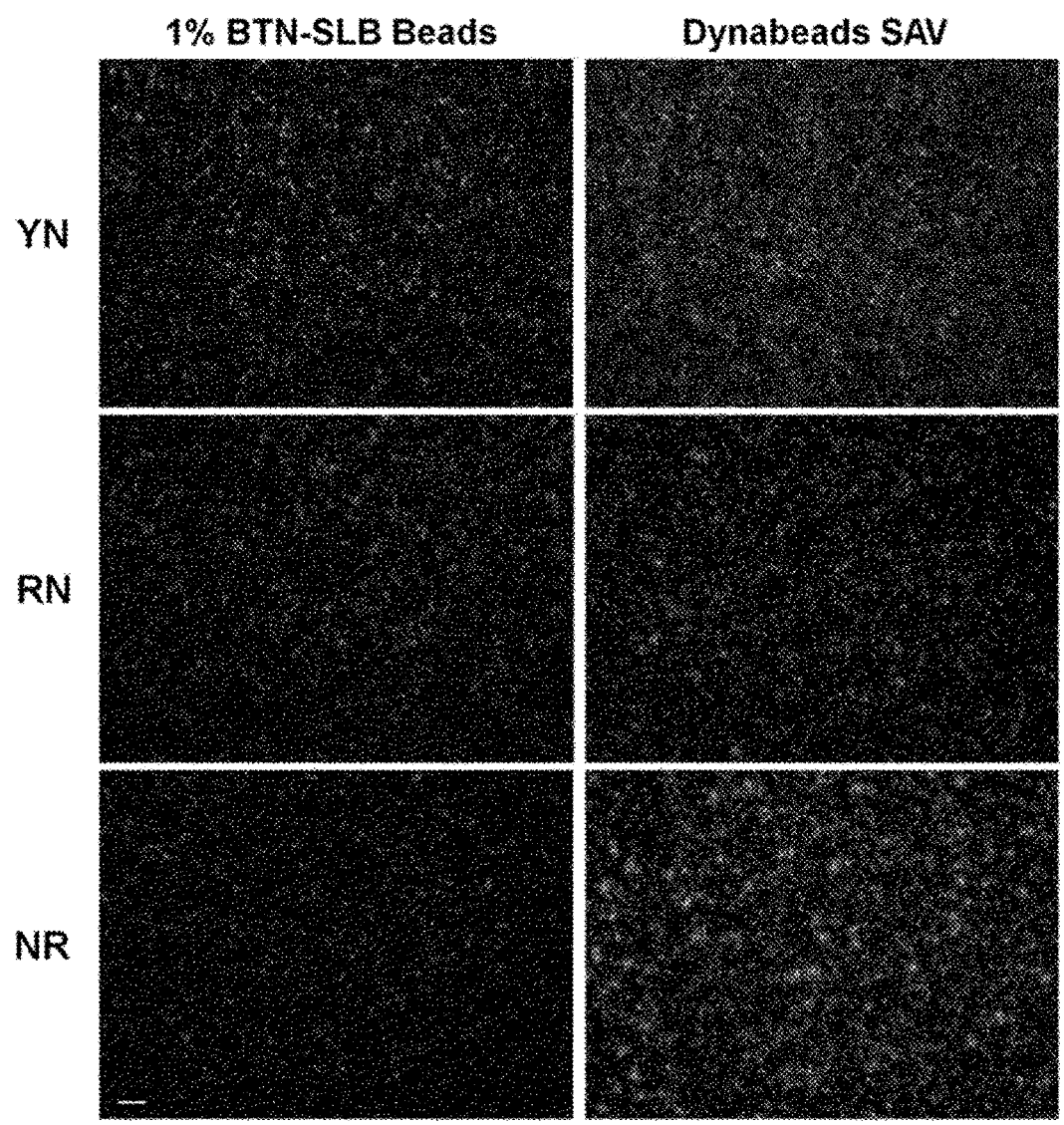

[FIG. 5]
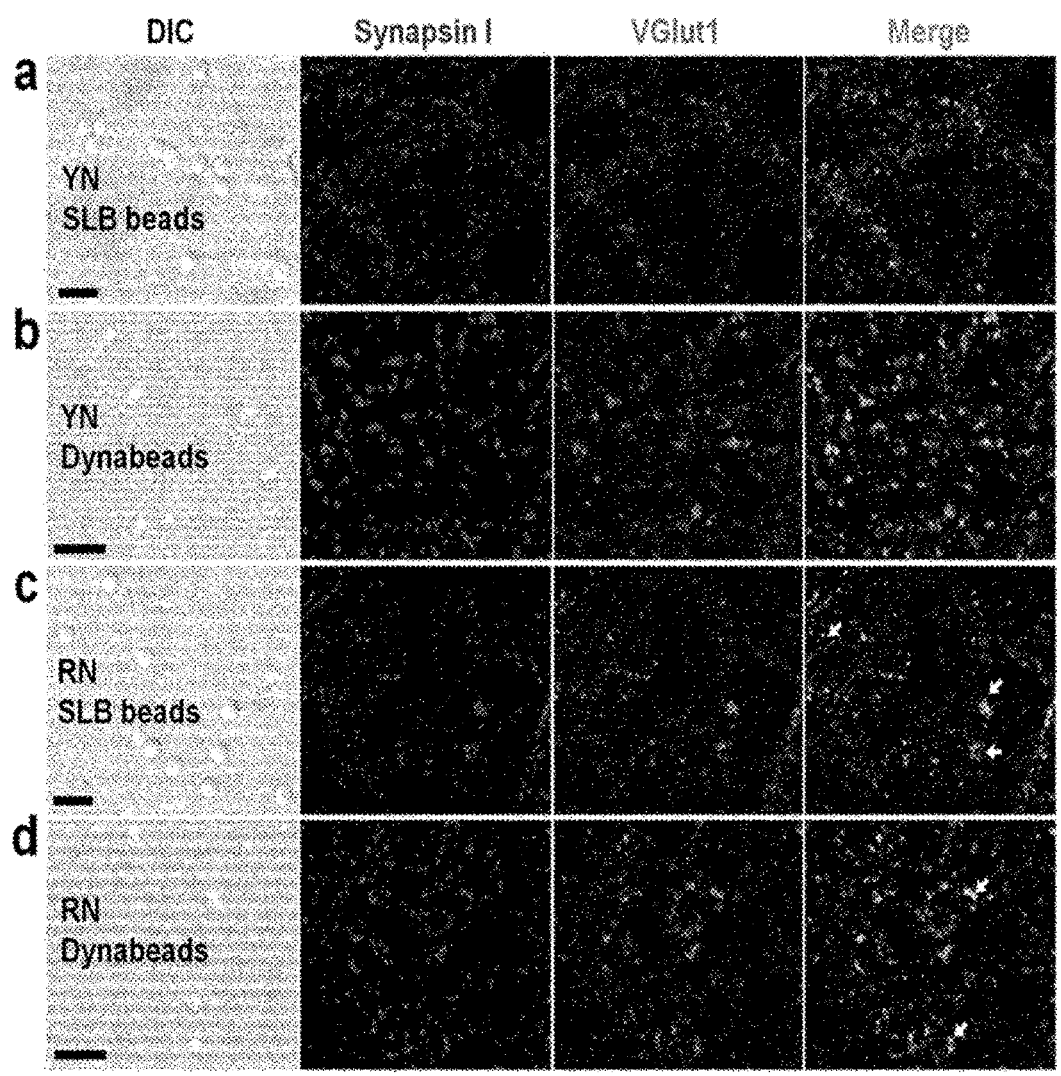

[FIG. 6]
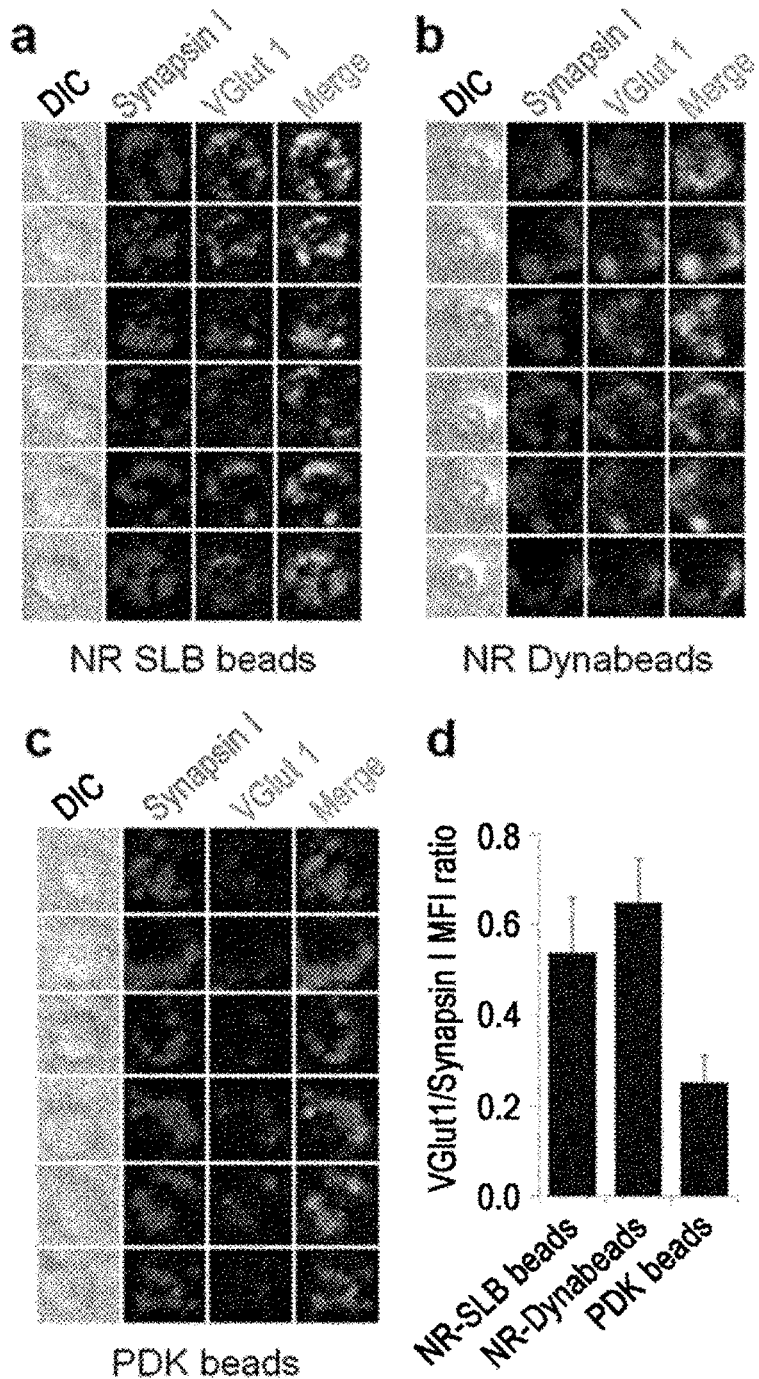

[FIG. 7]
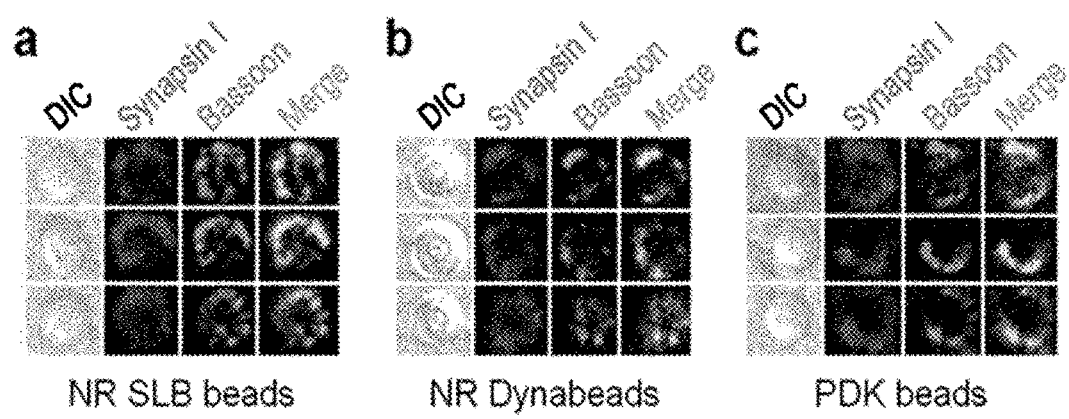

[FIG. 8]
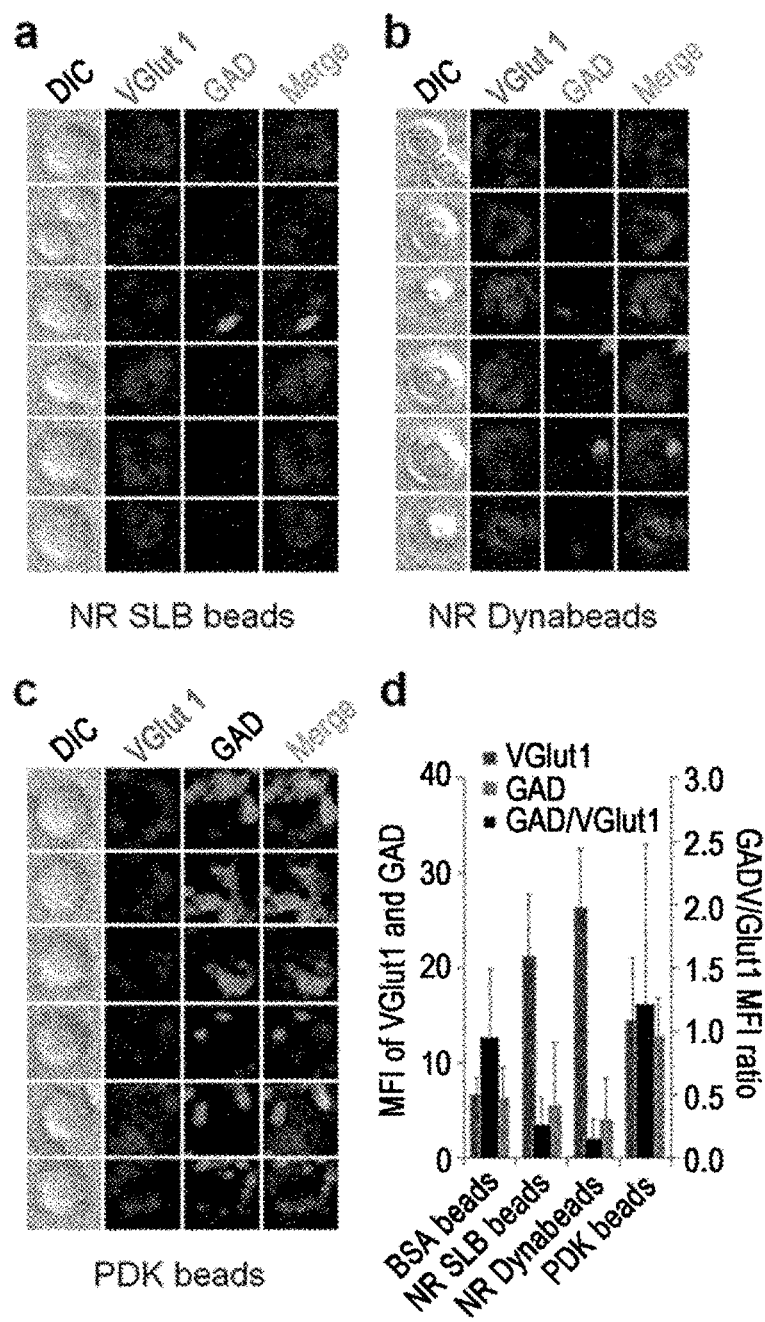

[FIG. 9]
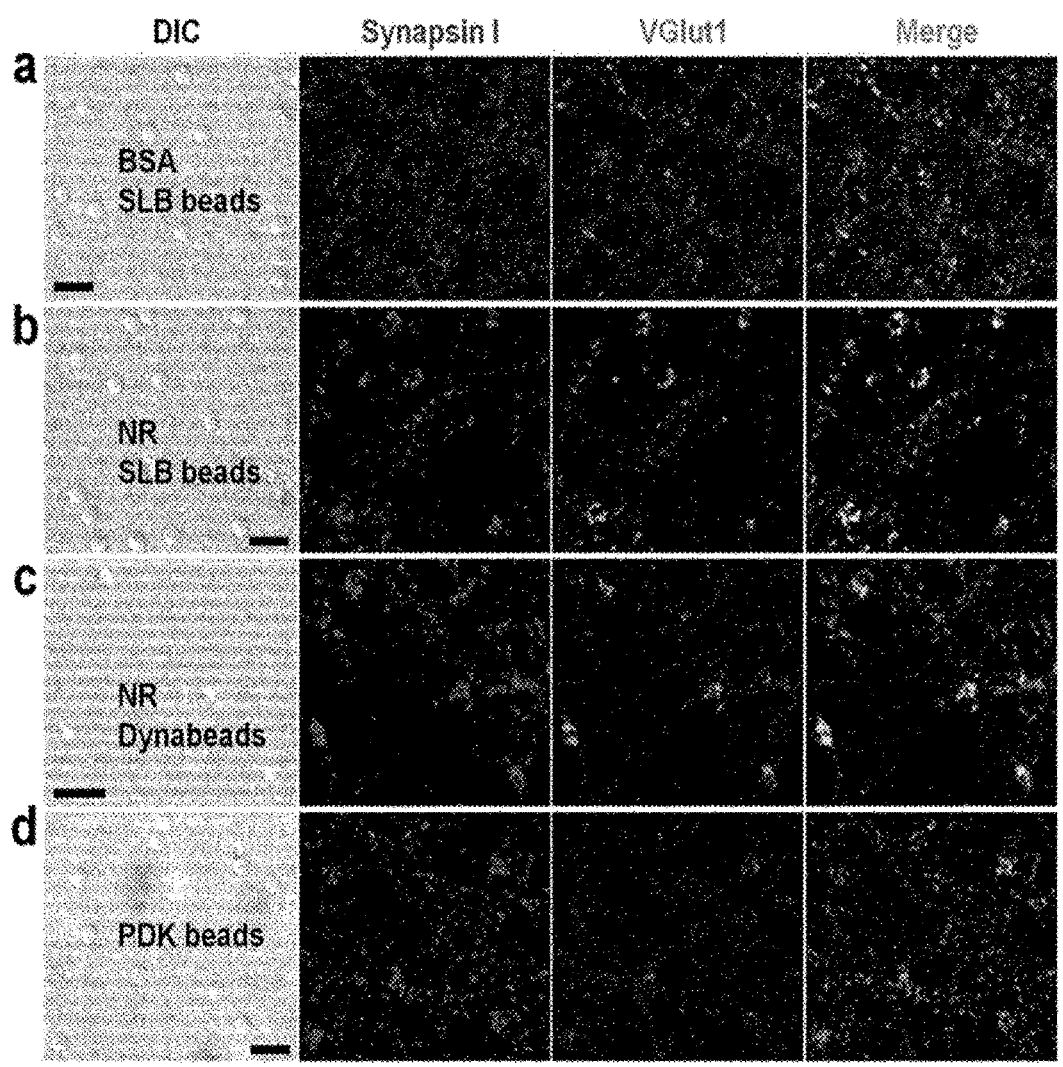

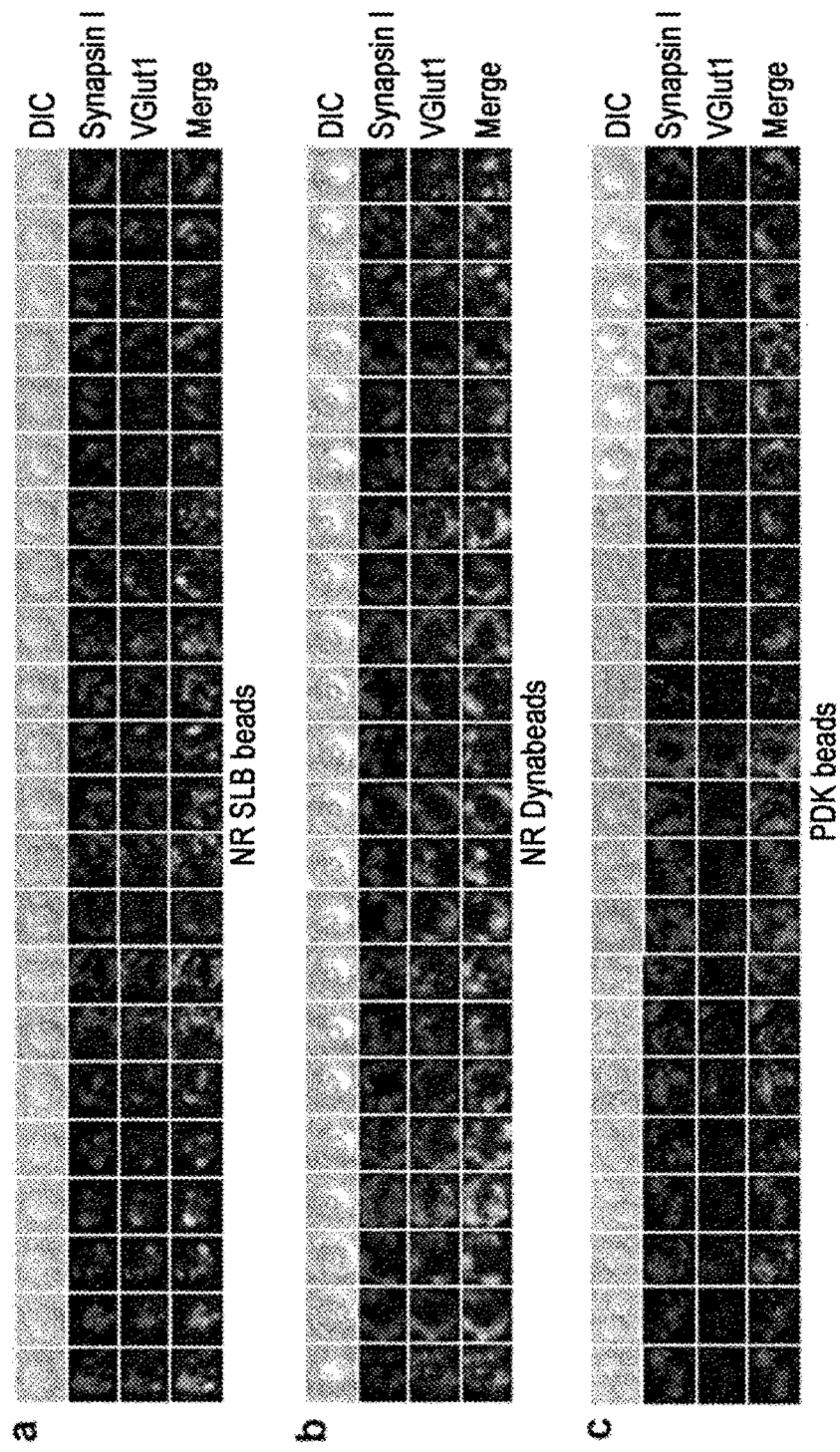
[FIG. 10]

[FIG. 11]
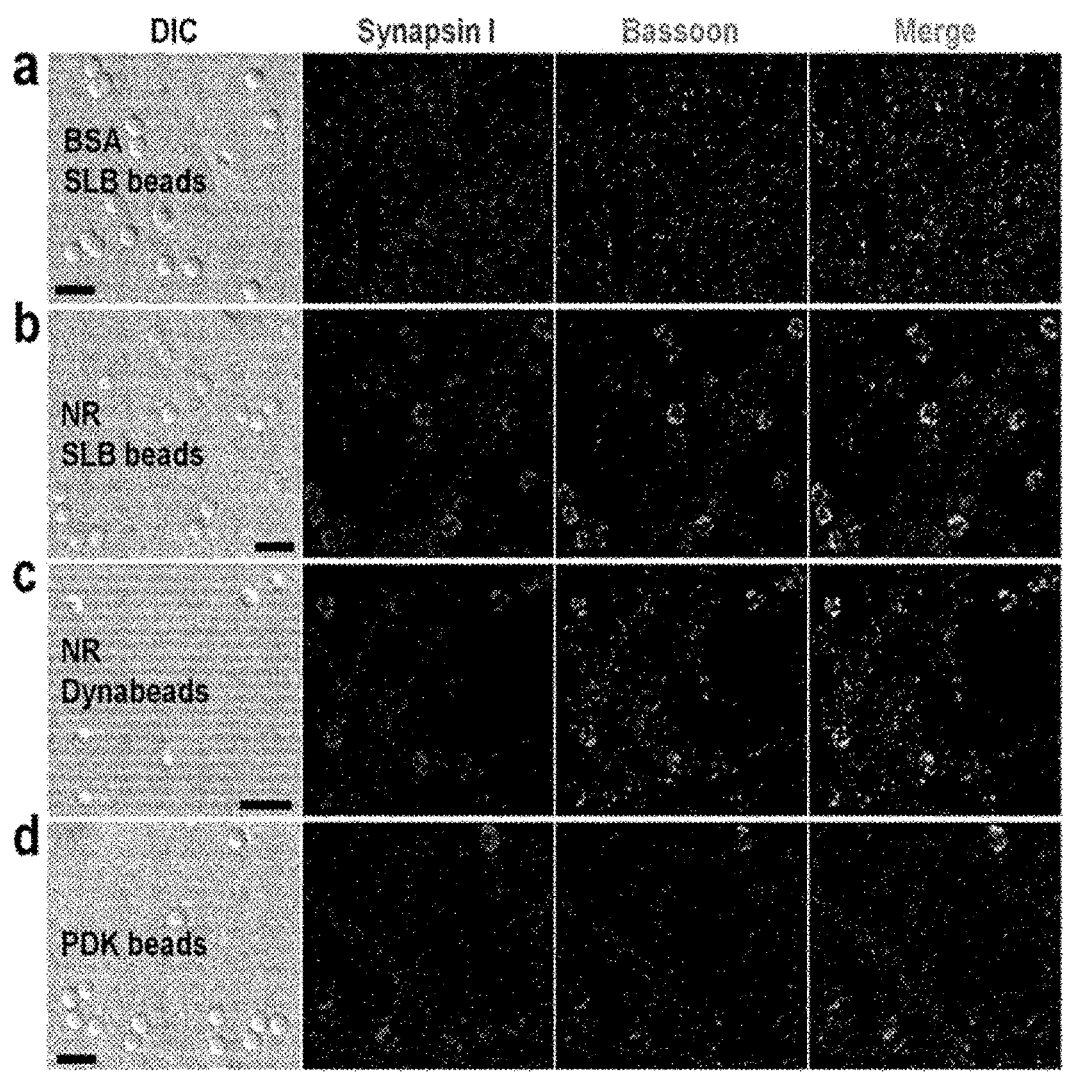

[FIG. 12]
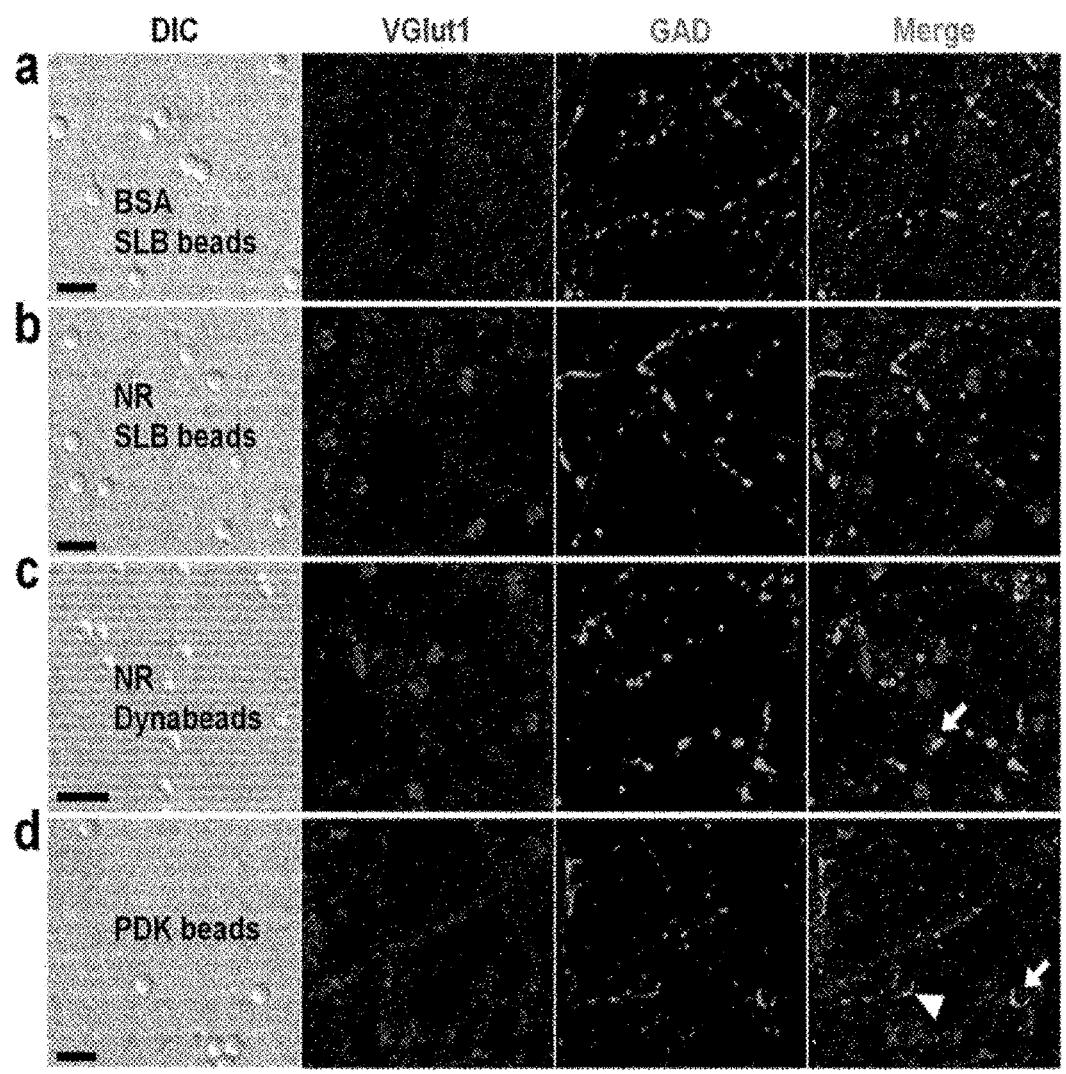

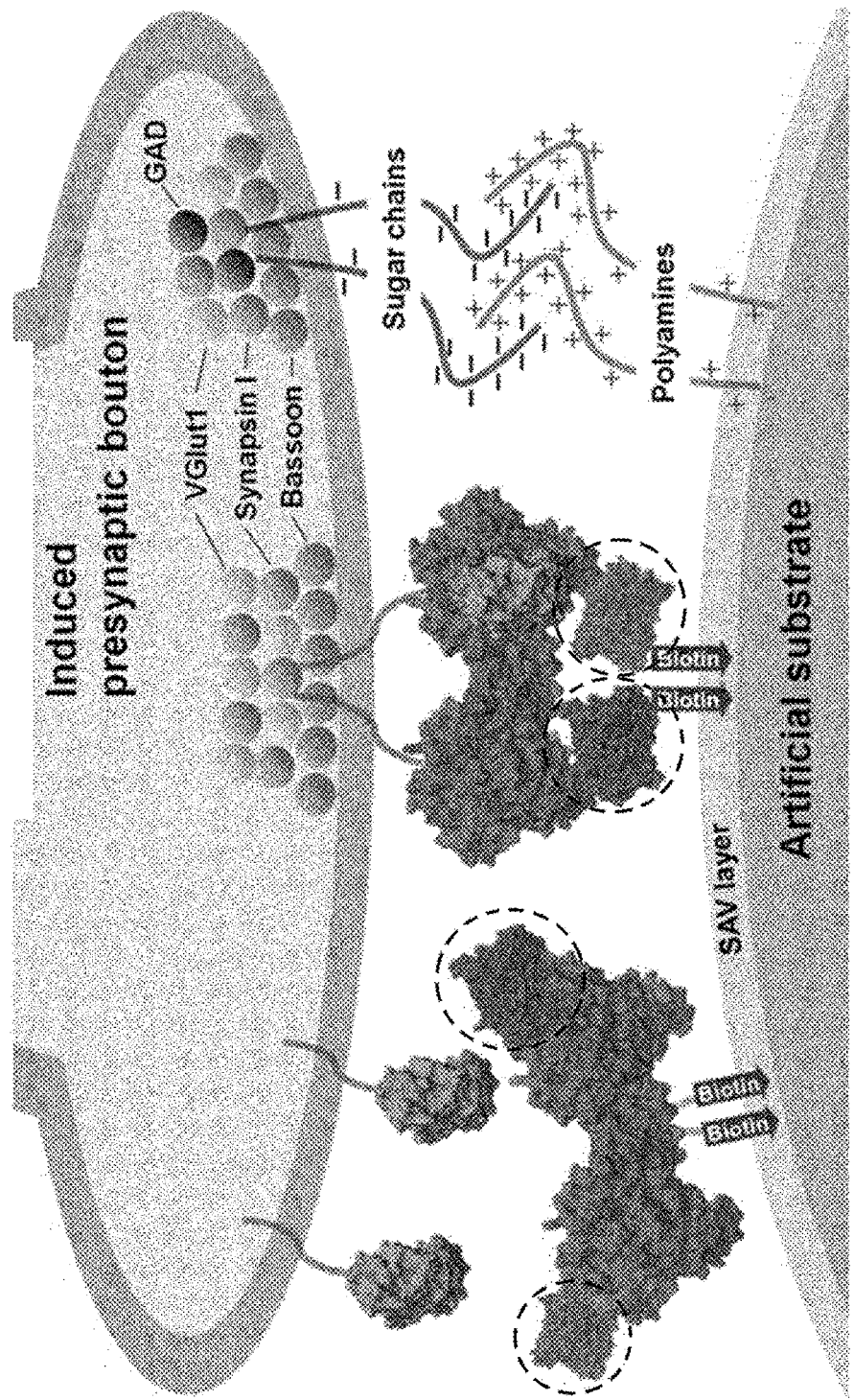
[FIG. 13]

[FIG. 14]
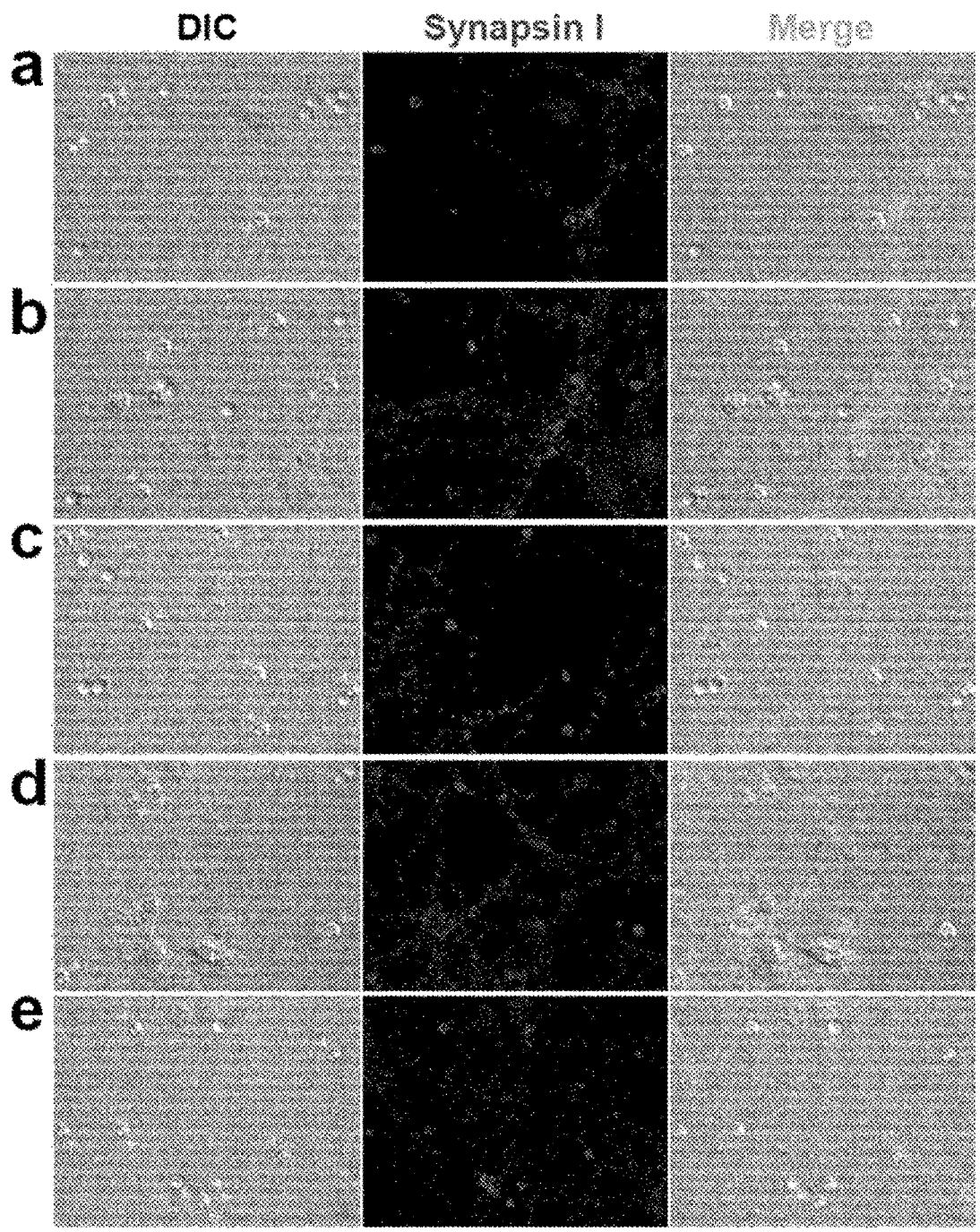

ARTIFICIAL SYNAPSE INDUCER AND METHOD OF MAKING THE SAME

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 29126843_1.TXT, the date of creation of the ASCII file is Sep. 27, 2018, and the size of the ASCII text file is 17 KB.

TECHNICAL FIELD

The present invention relates to a complex comprising a polypeptide comprising an extracellular domain of a synaptogenic protein; and biotin tagged at the C-terminus thereof; an artificial synapse inducer, in which the above complex is attached to a substrate coated with streptavidin (SAV); and a method for preparing a presynaptic differentiation-induced neuron comprising culturing a neuron in a medium comprising the artificial synapse inducer.

BACKGROUND ART

Neurons convey information electrically and chemically in a highly-organized system. Electrical impulses, known as action potentials ("AP", hereinafter), traveling along axons converge at presynaptic terminals and are converted into chemical signals, which are neurotransmitters. However, not all the transmitted APs trigger neurotransmitter release at the synaptic junctions, and not all the released neurotransmitters effectively induce postsynaptic APs. Unlike excitatory synapses, at the inhibitory synapses, APs are sequestered for the purpose of orchestration of overall network communication. Therefore, it is essential to distinguish between the excitatory and inhibitory signals in order to understand, mimic, and monitor neural network behavior.

In biological systems, excitatory and inhibitory synapses are determined by synaptic cell adhesion molecules ("CAMs", hereinafter). Among the interactions between the synaptic CAMs, the trans-synaptic adhesion between postsynaptic neuroligins ("Nlgs", hereinafter) and presynaptic neurexins ("Nrxs", hereinafter) is most representative and has been most extensively studied. Scheiffele et al. showed that the Nlgs expressed in non-neuronal cells were sufficient to induce presynaptic differentiation by introduction of presynaptic Nrxs. Furthermore, purified Nlg-1, whose transmembrane domain (TMD) is swapped with glycosylphosphatidylinositol (GPI)-anchoring motif, can successfully induce presynaptic differentiation when docked on glass microbeads that were coated with supported lipid bilayer (SLB) membranes. However, the chemical conjugation of Nlg-1 on polystyrene beads, despite its capability of adhering to Nrx-expressing cells, failed to induce presynaptic differentiation, suggesting that Nlg-1 requires a fluidic lipid bilayer environment for its activity. Additionally, the Nlg-1 is known to form a dimer.

DISCLOSURE

Technical Problem

The present inventors have studied a method for establishing an excitatory artificial synapse via an orientation-controlled immobilization of a synaptogenic protein on a substrate without a lipid bilayer. As a result, they have discovered that a synaptogenic protein, e.g., a protein complex in which biotin is tagged at the C-terminus of Nlg-1, can be immobilized on a substrate in a constant orientation by a SAV-biotin conjugation without the help of a lipid bilayer, and the thus-immobilized Nlg-1 can maintain its activity while being present in the form of a dimer as is in vivo, and thus can form an artificial synapse by inducing an excitatory presynaptic differentiation, thereby completing the present invention.

Technical Solution

An object of the present invention is to provide a complex comprising a polypeptide comprising an extracellular domain of a synaptogenic protein; and biotin tagged at the C-terminus of the polypeptide.

Another object of the present invention is to provide an artificial synapse inducer, in which the above complex is attached to a substrate coated with SAV.

A further object of the present invention is to provide a method for preparing a presynaptic differentiation-induced neuron comprising culturing a neuron in a medium comprising the artificial synapse inducer.

Advantageous Effects of the Invention

The complex of the present invention, which is tagged with biotin at the C-terminus of a polypeptide containing an extracellular domain of a synaptogenic protein, such as Nlg-1, can exhibit its activity by being attached to a substrate coated with SAV, thereby enabling the control of its orientation without the help of a lipid bilayer. Additionally, when the complex further includes RFP between the extracellular domain of a synaptogenic protein and biotin, it can not only facilitate its mass-production, quantification, and tracking but also exhibit the activity of a normal synaptogenic protein. Accordingly, the complex can induce an effective and excitatory or inhibitory synapse differentiation by addition thereof into a nerve cell culture after being immobilized on a substrate, and thus can be used as an artificial synapse inducer.

BRIEF DESCRIPTION OF THE DRAWINGS

FIG. 1a shows a 3-dimensional crystal structure of a neuroligin-1 (Nlg-1) dimer and neurexins (Nrx) complex. As shown on the left, Nrx is planted on the presynaptic membrane while Nlg-1 on the postsynaptic membrane. On the right, the structure of the two central α-helices required for Nlg-1 dimerization is shown.

FIG. 1b shows a schematic diagram of a plasmid constitution for the preparation of an Nlg-1 complex used in the present invention, which contains a fluorescence protein and/or biotin. In the figure, HA indicates HA tag; H6, hexa-His tag; OG, O-glycosylation-rich domain; TMD, transmembrane domain; CD, cytoplasmic domain; GPI, GPI-anchoring motif; GS, glycine-serine linker; and AP, biotin acceptor peptide or AviTag.

FIG. 2 shows pictures illustrating western blot profiles for the purification of an Nlg-1 complex to which a fluorescent protein, etc., is conjugated. YFP-Nlg-1-GPI, which is Nlg-1 tagged with YFP at the N-terminus and tagged with GPI at the C-terminus, rarely appeared in the elution fraction despite its presence in total cell lysate. When the GPI motif was replaced with AP, the YFP-Nlg-1-AP was secreted into the culture medium and retained in Ni-NTA resin. Both in vitro and in vivo biotinylation using BirA enzyme revealed biotinylated Nlg-1, regardless of the position of fluorescence proteins, YFP and RFP. An asterisk corresponds to the size of the Nlg-1 complex. A dagger corresponds to the non-specific binding of SAV-HRP to albumin in the culture medium. A double dagger indicates externally added BirA enzyme. RN, RFP-Nlg-1-AP; NR, N1 g-1-RFP-AP.

FIG. 3 shows a picture illustrating the quantification of Nlg-1-RFP-AP using electrophoresis and western blot. A known amount of BSA was loaded and compared with a known volume of an Nlg-1-RFP-AP elution fraction to yield Nlg-1 concentration (left panel). The biotinylated band was verified using western blot (right panel). The correlation between the fluorescence intensity and the concentration of Nlg-1-RFP-AP was also exhibited.

FIG. 4 shows pictures illustrating the reconstitution of fluorescent and biotinylated Nlg-1 on a biotin-functionalized SLB membrane and Dynabeads SAV. YN indicates YFP-Nlg1-AP; RN, RFP-Nlg-1-AP; NR, Nlg-1-RFP-AP. Scale bar=100 µm.

FIG. 5 shows pictures illustrating that the N-terminally tagged YFP in Nlg-1 on SLB beads (a) and Dynabeads (b) exerted negligible functionality in terms of synapsin I and VGlut1 aggregation. Replacing YFP with photostable, monomeric TagRFP-T slightly improved the Nlg-1 activity ((c) and (d), arrows). Scale bar=10 µm.

FIG. 6 shows pictures illustrating the presynaptic differentiation induced on artificial substrates containing beads coated with Nlg-1 complex according to the present invention. SLB beads coated with Nlg-1 complex and Dynabeads coated with SAV were used as experimental groups, and PDK beads (poly-D-lysine beads) were used as a comparative group. Nlg-1-RFP-AP (NR) immobilized on SLB beads (a) and Dynabeads SAV (b), and PDK-coated beads (c) recruited synapsin I and VGlut1 and assembled around the beads. (d) shows a graph illustrating the ratio of mean fluorescence intensity (MFI) between VGlut1 and synapsin I measured in the same region of interest (ROI) around the beads.

FIG. 7 shows pictures illustrating the presynaptic differentiation induced on artificial substrates containing beads coated with an Nlg-1 complex according to the present invention. SLB beads coated with the Nlg-1 complex and Dynabeads SAV were used as experimental groups, and PDK beads were used as a comparative group. (a) to (c) show pictures respectively illustrating the expression of synapsin I and Bassoon in each experimental group and control group, and they show that the enhanced synapsin I immunofluorescence puncta always colocalize with Bassoon-positive puncta.

FIG. 8 shows pictures illustrating the presynaptic differentiation induced on artificial substrates containing beads coated with an Nlg-1 complex according to the present invention. SLB beads coated with the Nlg-1 complex and Dynabeads SAV were used as experimental groups, and PDK beads were used as a comparative group. (a) to (c) show pictures respectively illustrating the comparison between excitatory and inhibitory presynaptic differentiations induced by NR SLB beads (a), NR Dynabeads SAV (b), and PDK beads (c). VGlut1 and GAD were used as markers for excitatory and inhibitory presynaptic differentiations, respectively. (d) shows a graph illustrating the ratio of mean fluorescence intensity (MFI) between GAD and VGlut1-positive puncta around the beads. The diameter of silica beads and Dynabeads was 5 µm and 2.8 µm, respectively.

FIG. 9 shows pictures illustrating the abilities for distinctly surface-treated beads to induce synapsin I and VGlut1. A complex C-terminally tagged with FRP regenerated Nla-1 activity both on SLB (b) and non-SLB membranes (c). PDK beads showed less frequent synapsin I- and VGlut1-positive fluorescence puncta (d). (a) shows the result from biotinylated BSA-coated beads as a negative control (scale bar=10 µm).

FIG. 10 shows pictures illustrating that the selected NR SLB beads (a) and NR Dynabeads (b) show synapsin I- and VGlut1-positive puncta. (c) PDK beads show weaker VGlut1-positive fluorescence puncta.

FIG. 11 shows pictures illustrating the verification of aggregated synapsin I aggregation as a positive presynapse marker. (a) shows a picture illustrating the measurement result of inactive biotinylated BSA on SLB beads, and (b) and (c) show the induction of both synapsin I and Bassoon due to NR, with the latter being nearer to the beads. (d) shows a picture illustrating the aggregation of the marker proteins by PDK beads, in which PDK beads show less frequent aggregation of the marker proteins. Scale bar=10 µm.

FIG. 12 shows pictures illustrating the preference for excitatory presynaptic differentiation of NR. (a) shows a picture illustrating the measurement result of SLB beads coated with inactive biotinylated BSA, as a negative control, showing background GAD puncta. (b) and (c) show the selectivity on excitatory presynaptic differentiation due to NR, in which NR induced VGlut1 but not GAD. (d) shows the measurement result of PDK beads, in which bead-shaped GAD-positive only puncta (arrow) and bead-shaped mixed puncta (arrowhead) were observed. Scale bar=10 µm.

FIG. 13 shows a schematic diagram illustrating a presynaptic differentiation mechanism induced by the Nlg-1 complex of the present invention and polybasic molecules. N-terminally tagged RFP (inside the dotted circles) may keep Nlg-1 (grey) from binding with Nrx (light grey), resulting in poor synaptogenesis at contacting neurites (left). An Nlg-1 complex with a C-terminal modification with RFP, in which the introduced RFP does not affect the interaction between an Nlg-1 dimer and Nrxs, can induce a successful excitatory presynaptic differentiation (middle). Additionally, both of the above two complexes can interact with Nrx of the contacting neurites through biotin conjugated to the C-terminus, without the supported lipid bilayer (SLB) membrane, by being immobilized on the artificial substrate coated with SAV in a uniform orientation. A differentiation-inducing mechanism by polybasic molecules such as PDK and PE is shown, and these materials can also induce presynaptic differentiation via the interaction with proteoglycans in negative charges, but they do not show any defined preference for excitatory synapses by an Nlg-1 complex and also have a lower differentiation-inducing efficiency (right).

FIG. 14 shows pictures illustrating the difference between the synapses being induced by Nlg-1 beads and PDK beads, which were added during different stages of neuron development, respectively. The pictures show fluorescence images of immunocytochemistry regarding synapse I of neurons differentiated for 18 days in vitro (18 DIV). (a) to (e) show neurons which were treated with Nlg-1 beads and PDK beads in cultivation at the 0 DIV, 7 DIV, 10 DIV, 14 DIV, and 17 DIV in vitro, respectively, and continuously developed until the 18 DIV, i.e., (a) to (e) represent neurons cultured by allowing them to come into contact with the beads added thereto for 18 days, 11 days, 8 days, 4 days, and 1 day. The beads indicated with an arrowhead with DIC images (left) are Nlg-1 beads, and the other beads are PDK beads.

EMBODIMENTS

In an aspect to accomplish the above objects, the present invention provides a complex comprising a polypeptide comprising an extracellular domain of a synaptogenic protein; and biotin tagged at the C-terminus of the polypeptide.

As used herein, the term "synaptogenic protein" collectively refers to all the proteins that can mediate the synaptogenesis by inducing the initial contact between an axon and a target cell thereof. The term synaptogenic protein, which may also be called synapse-forming protein, will be used in the present invention. The synaptogenic protein is involved in the introduction and organization of presynaptic and postsynaptic proteins required for synaptic transmission. For example, the synaptogenic proteins such as neuroligin, leucine-rich repeat transmembrane protein (LRRTM), netrin G ligand (NGL), synaptic cell adhesion molecule (SynCAM), ephrin-B receptor (EphB), and Slit- and Trk-like proteins (Slitrk), which are present postsynaptically, can induce presynaptic differentiation. Meanwhile, synaptogenic proteins such as neurexin, leukocyte common antigen-related protein (LAR), and netrin G, which are present presynaptically, can induce postsynaptic differentiation. Preferably, the synaptogenic protein may be Nlg, Nrx, LRRTM, NGL, SynCAM, EphB, LAR, netrin G, or Slitrk, and more preferably Nlg-1, but is not limited thereto. The synaptogenic proteins commonly include a target-binding site in the N-terminal direction while having a transmembrane domain in the C-terminal direction. That is, the N-terminus includes an extracellular domain which exhibits an activity and the C-terminus includes a transmembrane domain which is attached to a cell membrane.

The present invention is characterized in that the synaptogenic protein can be fixed to a substrate by the SAV-biotin binding while maintaining the intrinsic activity of the synaptogenic protein by conjugating biotin to the C-terminus of the extracellular domain of the synaptogenic protein. This complex can induce an excitatory or inhibitory synaptic differentiation when it is used in cultivation of neuron in the form being fixed to SAV, which is coated on the substrate via biotin conjugated to the C-terminus. Additionally, this complex does not require a lipid bilayer, which was conventionally introduced for the controlled orientation of the synaptogenic protein, and it can also remove a transmembrane domain, etc., as long as it includes an extracellular domain capable of exhibiting the activity of the synaptogenic protein.

For example, the complex according to the present invention is characterized in that it includes an extracellular domain of Nlg-1, which is a protein mediating the formation of a synapse between neurons, and its C-terminus is conjugated to biotin, and it is thus capable of being fixed on the artificial substrate coated with SAV via the biotin conjugated to the C-terminus to thereby have a controlled orientation.

As used herein, the term "neuroligin-1 (Nlg-1)" refers to a type I membrane protein which is present in the postsynaptic membrane and mediates the formation of a synapse between neurons. Nlg mediates signaling through synapses and affects the properties of a neural network by specifying synaptic functions. An alteration in genes encoding Nlgs in humans may result in autism and other cognitive disorders. This suggests that the expression of Nlg can induce presynaptic differentiation, which is mediated by the contact, at axons contacted thereto. The extracellular domain of Nlg mostly consists of a region that is homologous to acetylcholinesterase (AChE), and the amino acids important for the catalysis in AChE are not conserved in Nlg, and thus Nlg lacks esterase activity. Additionally, the AChE homologous region is crucial for the proper function of Nlg. Nlgs act as ligands for β-Nrxs which are located presynaptically. Nlg and β-Nrx "shake hands", resulting in the connection between two neurons and the production of a synapse. Nlgs also act in honeybees and their functions in insects are similar to those of vertebrates. Nlg dysfunction has been implicated in autistic spectrum disorders.

As used herein, the term "neurexin (Nrx)" refers to a presynaptic protein that helps to connect neurons at the synapse. Nrx is a type I membrane protein and classified into two kinds, α-Nrx and β-Nrx. The α-Nrxs are the larger of the two and have a different amino-terminal extracellular sequence. Nrx mediates signaling across synapses, and affects the properties of a neural network by specifying the synaptic functions. An alteration in genes encoding neurexin in humans may induce autism and other cognitive disorders. The β-Nrxs located presynaptically act as receptors for neuroligins located postsynaptically. As described above, Nlgs and β-Nrx "shake hands", resulting in the connection between two neurons and the production of a synapse. Additionally, β-Nrxs are involved in angiogenesis.

As used herein, the term "leucine-rich repeat transmembrane protein (LRRTM)" refers to a protein which recognizes the protein labeling present on the surfaces of other neurons. Numerous cells can specifically form synapses with the constituting components at particular subcellular levels of target cells. During this process, the LRRTM can recognize particular proteins, similar to a specific antigen-antibody recognition in an immune response, thereby enabling the recognition of target cells.

As used herein, the term "netrin G" refers to a protein immobilized on an axonal membrane by glycosylphosphatidylinositol (GPI), and vertebrates have its isoforms, netrin-G1 and netrin-G2.

As used herein, the term "netrin G ligand (NGL)" refers to a ligand which specifically binds to netrin G, and it is located on the postsynaptic membrane and interacts with presynaptic netrin G. Netrin G and NGL thereof serve as a modulatory signaling system to synapses, and thus any deficiency thereof may lead to behavioral defects.

As used herein, the term "synaptic cell adhesion molecule (SynCAM)" refers to a hemophilic protein which includes the transmembrane Ig-domain, also known as TSLC1, Sg1GSF, or IGSF4, and includes an intracellular PDZ protein-binding motif. Originally, it was identified as a tumor-inhibiting factor against small lung cell carcinoma, but it is now known to be mainly involved in intracellular adhesion and formation of synapses. Most SynCAMs are located on the synapses where the assembly and differentiation of synapses start through the central nervous system.

As used herein, the term "ephrin-B receptor (EphB)" refers to a receptor protein which interacts with ephrin-B, i.e., a ligand family thereof, and is activated by binding to ephrin-B. The ephrin-B is a subfamily of the Eph tyrosine kinase receptor family, which is composed of six members of EphB1 to EphB6. The extracellular domain of ephrin receptors includes a cysteine-rich region, two fibronectin type III domains, and a highly conserved globular ephrin ligand-binding domain, and the cytoplasmic domain includes two conserved tyrosine residues, a tyrosine kinase domain, a sterile alpha motif (SAM), and a juxtamembrane region having a PDZ-binding motif.

As used herein, the term "Slit- and Trk-like proteins (Slitrk)" refers to a neural transmembrane protein, which regulates the growth of neuritis, and it s a kind of a synapse organizer. The Slitrks are abundantly present in postsynaptic densities and their overexpression promotes the formation of synapses. The Slitrks are known to be involved in the formation of both excitatory and inhibitory synapses in an isoform-dependent manner. Additionally, Slitrks, along with leukocyte antigen-related receptor protein tyrosine phosphatase (LAR-RPTP) family members, maintain the formation of synapses so that the excitatory-inhibitory balance can be harmonized.

As used herein, the term "biotin" refers to a water-soluble vitamin B (vitamin $B_7$), which is also called vitamin H or coenzyme R. Biotin consists of a ureido (tetrahydroimidizalone) ring fused with a tetrahydrothiophene ring. Biotin contains valeric acid bound to a carbon atom of the tetrahydrothiophene ring. Biotin is a cofactor for carboxylase and is involved in the syntheses of fatty acids, isoleucine, and valine, and gluconeogenesis. Biotin, in addition to its characteristic as a cofactor described above, has the characteristics of strongly binding to proteins, such as avidin, SAV, and neutravidin (or deglycosylated avidin), with a dissociation constant $K_d$ at the level of $10^{-14}$ M to $10^{-15}$ M. In particular, since the specific binding of biotin with SAV can be maintained in harsh conditions, the SAV-biotin binding has been applied in various bioengineering fields. Due to the small size of biotin, it does not affect on the activities of proteins comprising the same and thus biotin is attached to various proteins to be used in biochemical assays, etc. This process, i.e., the process of attaching biotin to proteins, is called biotinylation. The biotinylated proteins can be immobilized on the beads by incubating the biotinylated proteins with SAV/avidin beads, etc.

As described above, the complex according to the present invention contains biotin attached to its C-terminus. The attachment of biotin to the C-terminus may be performed using any method known in the art without limitation. For example, the above complex may be prepared in vivo production and secretion in a state where biotin is attached to the C-terminus of the complex, or via in vitro biotinylation after in vivo production and secretion in a state where a biotin acceptor peptide, e.g., AP or AviTag, is tagged.

Preferably, the complex according to the present invention may comprise an extracellular domain of Nlg-1 having an amino acid sequence represented by SEQ ID NO: 1. However, the amino acid sequence is not limited by the native amino acid sequence of SEQ ID NO: 1, but any mutein of the native amino acid sequence or a fragment thereof may be included, as long as they can exhibit an activity as Nlg-1, for example, as long as they can induce synaptic differentiation. As used herein, the term "mutein" refers to a protein with an amino acid sequence altered by deletion, addition, non-conservative or conservative substitution, or a combination thereof in at least one amino acid residue of a given native amino acid sequence. It is obvious that this can be equally applied to synaptogenic proteins other than Nlg-1. The amino acid sequence of SEQ ID NO: 11 is a C-terminus portion of SEQ ID NO: 1 such that the C-terminus amino acid (the 683 position) of SEQ ID NO: 1 is the C-terminus amino acid (the 213 position) of SEQ ID NO: 11.

The complex according to the present invention may further comprise a fluorescent protein, and the fluorescent protein may be comprised in the sequential order of a polypeptide comprising an extracellular domain of a synaptogenic protein, a fluorescent protein, and biotin from its N-terminus. The use of the fluorescent protein enables purification, quantification, and tracking of the complex according to the present invention.

As used herein, the term "fluorescent protein" refers to a member of a class structurally corresponding to proteins which commonly share self-sufficient intrinsic characteristics and are capable of forming chromophores with wavelengths of visible light from three amino acid sequences within their polypeptide sequences. Localization of a gene product and dynamics can be visualized using a fluorescence microscope by introducing a gene (or a chimeric gene) into a live cell and allowing it to encode an engineered fluorescent protein. Accordingly, the fluorescent proteins are effectively used in numerous bioengineering studies. As described above, fluorescent proteins are most frequently used in research for imaging of the localization and dynamics of particular organelles or recombinant proteins in a live cell. For the visualization of particular organelles, a gene encoding a fluorescent protein may be fused to a cDNA encoding a protein or peptide which is known to be localized in particular organelles to be observed, using a standard molecular biology technique. The fusion can be performed by forming a covalent link between a target motif and a fluorescent protein and expressing the chimeric gene as a single polypeptide. A mammalian cell may be transfected with a chimeric gene-containing plasmid under an appropriate promoter in order to express the chimeric gene and produce the corresponding protein. The chimera is set to be located on the target organelles so that the target organelles can emit fluorescence. Accordingly, the shapes, dynamics, and distribution of organelles can be represented as a function of time using a fluorescence microscope. Additionally, information on multiple organelles can be obtained simultaneously using fluorescent proteins of various colors.

Preferably, the fluorescent protein may be blue fluorescent protein (BFP), enhanced blue fluorescent protein (eBFP), cyan fluorescent protein (CFP), enhanced cyan fluorescent protein (eCFP), green fluorescent protein (GFP), enhanced green fluorescent protein (eGFP), yellow fluorescent protein (YFP), enhanced yellow fluorescent protein (eYFP), or red fluorescent protein (RFP). Some of these fluorescent proteins require a high energy source close to that of UV rays for the excitation. However, high energy light has low transmittance. Therefore, when the light is applied in cells, it may cause harmful effects such as genetic mutations, or it may cause adverse effects on cells through the products generated by photoreactions. Meanwhile, some fluorescent proteins may tend to show multimerization of dimers or more. However, for some fluorescent proteins with a high tendency to multimerize, the multimerization may affect the orientation or activities of synaptogenic proteins, and thus it is preferable to use fluorescent proteins with a low tendency to multimerize. Accordingly, the fluorescent protein may be YFP or RFP, but is not limited thereto, and most preferably, the fluorescent protein may be RFP.

The complex according to the present invention may further comprise a polyhistidine-tag (His-tag) or an influenza hemagglutinin epitope tag (HA-tag) for its separation and purification.

According to a specific embodiment of the present invention, when a fluorescent protein is located in the N-terminal direction of Nlg-1, it may inhibit Nlg-1 from forming a synapse by blocking binding Nlg-1 to Nrx. However, when the fluorescent protein was introduced into the C-terminal direction, it was confirmed that the differentiation of neurons could be normally induced by Nlg-1 (FIG. 13).

In another aspect, the present invention provides an artificial synapse inducer in which the above complex is attached to a substrate coated with a biotin-binding protein.

As used herein, the term "biotin-binding protein" refers to a protein which can specifically bind to biotin with high binding affinity. Since the biotin-binding protein has high specificity to biotin, it has a low level of non-specific binding. Regarding the binding to biotin, the biotin-binding has a dissociation constant of $10^{14}$ M to $10^{15}$ M, and thus it can maintain the binding under very harsh conditions. The biotin-binding protein is a tetramer and each protein molecule can maximally bind to four biotin molecules.

Preferably, the biotin-binding protein may be an avidin-like proteins such as SAV, traptavidin, or neutravidin, but any protein may be used without limitation, as long as it can specifically bind to biotin.

As used herein, the term "avidin" refers to a biotin-binding protein which is considered to act as an antibiotic in eggs of birds, reptiles, and amphibians. In the case of chicken avidin, it has a molecular weight of 67 kDa to 68 kDa, is formed from four small units consisting of 128 amino acids, respectively, and each small unit can bind to a single biotin molecule. Since the avidin is highly glycosylated, it contains carbohydrates in the amount of 10% of the total mass, has a basic isoelectric point (pI) from 10 to 10.5, and has high solubility in water and aqueous salt solutions.

As used herein, the term "SAV" refers to a tetramer biotin-binding protein with a molecular weight of 60 kDa, which is separated from *Streptomyces avidinii*. SAV has a very low homology with avidin, but their structures are very similar to each other. SAV has an antibiotic activity, as is the case with avidin, and has very high binding affinity to biotin. Meanwhile, unlike avidin, SAV does not contain carbohydrates, has an acidic isoelectric point (pI=5), and has a significantly lower solubility compared to that of avidin. Commercially available SAV, e.g., Thermo Scientific Pierce SAV, is SAV in a recombinant form with a molecular weight of 53 kDa having an isoelectric point close to neutral (pI=6.8 to 7.5). The lack of glycosylation and low pI of SAV result in a low level of non-specific binding (in particular, lectin binding) compared to that of avidin. Due to these characteristics, SAV is selected as an ideal reagent for many detection systems.

As used herein, the term "traptavidin" refers to a variant or mutein of SAV which has an about 10 times slower dissociation rate to biotin, increased mechanical strength, and improved thermal stability. Traptavidin also binds specifically to biotin.

As used herein, the term "neutravidin", also called deglycosylated avidin, refers to a protein prepared for the purpose of resolving the major drawbacks of native avidin and SAV. As presented in its name, it is a protein prepared by the deglycosylation of avidin, and which maintains high binding affinity to biotin while having a reduced molecular weight (60 kDa) compared to that of avidin. The deglycosylation of avidin reduces the lectin binding to an undetectable level and lowers the isoelectric point (pI=6.3), thereby effectively removing the major causes of non-specific binding to avidin. Since lysine residues are maintained in a usable state, neutravidin can be easily derivatized or complexed, as is the case with SAV. Additionally, since neutravidin exhibits high binding affinity to biotin and a low non-specific binding, it can be used variously as an ideal biotin-binding protein.

As used herein, the term "substrate" may refer to a material in solid phase with a predetermined shape, which can support the complex according to the present invention to be immobilized thereto. The materials to be used as the substrate may include silicone, glass, metals, magnetic materials, semi-conductors, ceramics, etc., without limitation. Additionally, the substrate may be modified on its surface to have reactivity, or further introduced with a layer of a new material. The shape of the substrate may be in various forms such as a sphere, plane, etc., but is not limited thereto. Preferably, the substrate may be the shape of in spherical microbeads having a diameter at the level of micrometers.

As used herein, the term "artificial synapse inducer" refers to a material which can induce synaptic differentiation of neurons in an in vitro condition, instead of an in vivo differentiation environment of neurons.

According to a specific embodiment of the present invention, it was confirmed that by culturing artificial synapse inducers according to the present invention, in which the Nlg-1 complex comprising biotin at its C-terminus was attached to microbeads along with neurons, synapsin I, which is a presynaptic marker protein, and vesicular glutamate transporter 1 (VGlut1) were introduced around the inducers to induce presynaptic differentiation (FIGS. 6a to 6d, and FIG. 9).

In another aspect, the present invention provides a method for preparing a presynaptic differentiation-induced neuron comprising culturing the neuron in a medium comprising the artificial synapse inducers.

Preferably, an excitatory presynaptic differentiation or an inhibitory presynaptic differentiation can be induced using the artificial synapse inducers according to the present invention. The selectivity on the differentiation direction varies according to the kinds of synaptogenic proteins introduced in the artificial synapse inducers.

As used herein, the term "an excitatory synapse" refers to a synapse in which an action potential in a presynaptic neuron increases the probability of occurrence of an action potential in a postsynaptic cell. Neurons form networks through which nerve impulses travel, each neuron making numerous connections with other neurons. These electrical signals may be excitatory or inhibitory, and, if the total of excitatory influences exceeds that of the inhibitory influences, the neuron may be stimulated. That is, a new action potential may be generated at its axon hillock, thereby transmitting the information to yet another cell. This phenomenon is known as an excitatory postsynaptic potential (EPSP). It may occur via direct contact between cells (i.e., via gap junctions), as in an electrical synapse, however, it most commonly occurs via the vesicular release of neurotransmitters from the presynaptic axon terminal into the synaptic cleft, as in a chemical synapse. The excitatory neurotransmitters then migrate via diffusion to the dendritic spine of the postsynaptic neuron and bind a specific transmembrane receptor protein that triggers the depolarization of the cell.

Meanwhile, as used herein, the term "an inhibitory synapse" refers to a synapse in which a nerve impulse in a presynaptic cell induces the release of inhibitory neurotransmitters that triggers the opening of multiple ion channels in the postsynaptic cell membrane so that negative ions move into (or positive ions move out of) the cell, thereby stabilizing its resting potential. One representative example of the inhibitory neurotransmitter is GABA.

The excitatory synapses play an important role in information processing within the brain and throughout the peripheral nervous system. Generally located on the dendritic spines, or neuronal membrane protrusions on which glutamate receptors and postsynaptic density (PSD) components are concentrated, the excitatory synapses aid in the electrical transmission of neuronal signals. The physical morphology of synapses is crucial in understanding their functions, and the inappropriate loss of synaptic stability leads to the disruption of neuronal circuits and the subsequent neurological diseases. Despite the presence of innumerable different causes for different neurodegenerative illnesses, such as genetic dispositions or mutations, normal aging process, parasitic and viral causes, etc., many can be traced back to dysfunctional signaling between the neurons themselves, often at the synapse. Excitatory mechanisms are involved in various conditions leading to neuronal damage, including hypoglycemia, trauma, stroke, seizures, and many neurodegenerative diseases, thus having important implications in disease treatment. Therefore, there is a need for the study to independently study the excitatory signaling and the inhibitory signaling in order to understand, mimic, and observe the behaviors of neuronal networks.

The selective synaptic differentiation trend according to the kinds of mutually interacting presynaptic and postsynaptic proteins are summarized in Table 1 below. For example, as shown in Table 1, an excitatory synaptic differentiation can be selectively induced when each of presynaptic β-Nrx, α-Nrx or β-Nrx (-SS4), netrin G-1 or netrin G-2, and LAR-RTPT interacts with postsynaptic Nlg-1, LRRTM 1 or LRRTM 2, NGL-1 or NGL-2, and NGL-3, respectively. Meanwhile, an inhibitory synaptic differentiation can be selectively induced when presynaptic PTP and postsynaptic Slitrk-3 interact with each other, and the excitatory synaptic differentiation and the inhibitory synaptic differentiation can be induced simultaneously when each of presynaptic α-Nrx and PTP interacts with postsynaptic Nlg-2 and Slitrk-1, -2, -4, -5, or -6, respectively. Accordingly, an artificial synapse inducer comprising an appropriate synaptogenic protein can be selected according to the direction of the synaptic differentiation to be induced.

TABLE 1

| Interactions between synapse-forming proteins | | Synapse | |
| --- | --- | --- | --- |
| Presynaptic | Postsynaptic | Excitatory | Inhibitory |
| β-Nrx | Nlg-1 | O | |
| α-Nrx | Nlg-2 | O | O |
| α-, β-Nrx (-SS4[1]) | LRRTM 1 and LRRTM 2 | O | |
| Netrin G-1, netrin G-2 | NGL-1 and NGL-2 | O | |
| LAR-RPTP[2] | NGL-3 | O | |
| PTP[3] | Slitrk-1, -2, -4, -5, and -6 | O | O |
| PTP[3] | Slitrk-3 | | O |

[1]SS4: Lack of splice site 4 (adhesion part 4)
[2]LAR-RPTP: Leukocyte antigen-related receptor protein tyrosine phosphatase
[3]PTP: Protein tyrosine phosphatase According to a specific embodiment of the present invention, when neurons are cultured along with artificial synapse inducers according to the present invention, in which the Nlg-1 complex comprising biotin at its C-terminus, immobilized to a lipid bilayer or the beads coated with SAV, synapsin I, which is a representative presynaptic marker, and VGlut1, which is an excitatory presynaptic marker protein, were shown to have positive responses. Additionally, they also showed strong positive responses to Bassoon, which labels the presynaptic active zone. Meanwhile, it was confirmed that GAD, which is a marker protein for an inhibitory γ-aminobutyric acid synapse, was not expressed. In contrast, the PDK beads, which are conventionally known to induce a presynaptic differentiation, were shown to significantly reduce the expression of VGlut1, which is an excitatory presynaptic marker, compared to when the inducers according to the present invention were used, and also shown to express GAD, an inhibitory presynaptic marker (FIGS. 6 to 8, and FIG. 10). This suggests that the artificial synapse inducers according to the present invention, which includes the Nlg-1 complex to which biotin is conjugated at its C-terminus, can be effectively used for inducing an excitatory presynaptic differentiation.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Materials

A plasmid encoding cholinesterase-like domain (CLD) of Nlg-1 followed by GPI anchoring motif (pNICE-HA-H6-Nlg-1-GPI) was provided by Dr. Peter Scheiffele. A plasmid carrying EYFP-tagged full length Nlg-1 (pNICE-YFP-Nlg-1) was provided by Dr. Ann Marie Craig. A TagRFP-T expressing plasmid (pcDNA3-TagRFP-T) was provided by Dr. Roger Y. Tsien. BirA plasmids (pDisplay-BirA-ER and pET21a-BirA) were purchased from Addgene (Cambridge, Mass.). Carbenicillin (Carb) was purchased from Gold Biotechnology (St. Louis, Mo.). Streptavidin (SAV), bovine serum albumin (BSA) (A3059), adenosine 5'-triphosphate (ATP), polyethyleneimine (Mw: 25,000), Kanamycin sulfate, and G418 (Geneticin) were purchased from Sigma-Aldrich (St. Louis, Mo.). QIAprep Spin Miniprep, QIAGEN Plasmid Plus Midi, QIAquick Gel Extraction, Phusion DNA polymerase, and Ni-NTA resin were purchased from Qiagen (Seoul, Korea). Restriction enzymes and T4 ligase were purchased from New England Biolabs (Ipswich, Mass.). Alexa-labeled secondary antibodies, bacterial cell line DH10B, mammalian cell line HEK293-H, neuronal cell culture media, SAV conjugated with horseradish peroxidase (SAV-HRP), Opti-MEM® I Reduced Serum Medium, Biocytin-Alexa 594, D-biotin, and Dynabeads® M-280 Streptavidin were purchased from Invitrogen (Carlsbad, Calif.). Silica beads (5 µm in diameter) were purchased from Bangs Laboratories, Inc. (Fishers, Ind.). Egg phosphatidylcholine (PC) and 1,2-dipalmitoyl-sn-glycero-3-phosphoethanolamine-N-(cap-biotinyl) (sodium salt) (Biotin-Cap-PE) were purchased from Avanti Polar Lipids (Alabaster, Al). Goat Nlg-1 polyclonal antibody (sc-14084) was purchased from Santa Cruz Biotechnology, Inc. (Santa Cruz, Calif.). Rabbit synapsin I monoclonal antibody (AB1543), guinea pig VGLUT1 polyclonal antibody (AB5905), and rabbit GAD65/67 antibody (AB1511) were purchased from Merck Millipore (Billerica, Mass.). Mouse Bassoon monoclonal antibody (ab82958) was purchased from Abcam (Cambridge, UK).

Example 2: Molecular Biology

The predicted O-glycosylation motif (OG), transmembrane domain (TMD), and cytosolic domain of Nlg-1, from Ser640 to the C-terminus, were replaced with a GS-linker followed by a 14-mer biotin acceptor peptide (AP or Avi-Tag). First, pNICE-YFP-Nlg-1 and the staggered PCR product from primers AP-1F (SEQ ID NO: 2), AP-2R (SEQ ID NO: 3), AP-3F (SEQ ID NO: 4), and AP-4R (SEQ ID NO: 5) were digested with KpnI and NotI, and ligated together. To aid purification, Hisx8 encoding primers, PvuI-H8-F (SEQ ID NO: 7), and PvuI-H8-R (SEQ ID NO: 8) were annealed, and introduced upstream of the YFP sequence using a single PvuI site, yielding pNHY-Nlg-1-AP. To replace YFP with monomeric RFP, TagRFP-T was PCR amplified from pcDNA3-TagRFP-T using primers PvuI-H8-TagRFP-T-F (SEQ ID NO: 9) and TagRFP-T-SalI-R (SEQ ID NO: 10), cut with PvuI and SalI, and ligated with pNHY-Nlg-1-AP that had been digested with the same restriction enzymes, resulting in pNHR-Nlg-1-AP. To introduce RFP after Nlg-1, new cloning sites, PvuI and SalI, were inserted within the GS linker using primers AP-1F, AP-2R, AP-PvuI-SalI-3F (SEQ ID NO: 6), and AP-4R. The staggered PCR product was then ligated with pNICE-HA-H6-Nlg-lab-GPI after restriction digest of both DNAs with KpnI and NotI, yielding pNHH-Nlg-1-AP. The TagRFP-T PCR product (see above) and pNHH-Nlg-1-AP were digested with PvuI and SalI followed by ligation to give pNHH-Nlg-1-R-AP. Bacterial expression and purification of bacterial BirA biotin ligase were conducted using pET21a-BirA plasmid. The primers used in the present invention are listed in Table 2 below.

temperature for 30 minutes and added to HEK293-H cells grown to about 20% confluence in a culture dish with a diameter of 10 cm at 37° C. DMEM medium was replaced after 4 hours of incubation. After three days, the cells were treated with G418 at a final concentration of 800 μg/mL. The G418 treatment was repeated with a fresh medium after two days. After two weeks, single colonies with brightest fluorescence signals were picked and seeded on a 24-well plate. Among them, the best fluorescent colonies were repeatedly selected until only one colony was left and the final best fluorescent colony was seeded on a culture dish with a diameter of 10 cm for the subsequent passage. The thus-established stable cell line was kept in a DMEM medium containing 100 μg/mL of G418.

Example 4: Preparation of Biotinylated Nlg-1 (Biotinylated Nlg-1)

The established HEK-293-H stable cell lines of expressing Nlg-1 were transfected with pDisplay-BirA-ER plasmid. Specifically, the plasmid pDisplay-BirA-ER (24 μg) dissolved in 1.5 mL of the Opti-MEM solution was mixed with 1.56 mL of an Opti-MEM solution containing 60 μg of PEI at 25° C. for 20 minutes. The mixture was added to the established HEK293-H stable cell lines at about 20% confluence in a culture dish with a diameter of 10 cm. After 4 hours of incubation, DMEM medium was replaced with a fresh one containing 100 μg/mL G418 and 10 μM biotin. The

TABLE 2

| Primer name | DNA oligomer sequence from 5' end (length/bp) | SEQ ID NO |
|---|---|---|
| AP-1F | GGCGGTGGTACCTCATCTGCATAATCTCAATGACATTGGCGGCGGC<u>AGCG GCGGAGGCAGCGAGGG</u> (66) | 2 |
| AP-2R | <u>GCCCTCGCTGCCGCCTCCGCTGCCGCCTCCGCTGCCTCCGCCCTCGCTGC CTCCGCCGCT</u> (60) | 3 |
| AP-3F | <u>GCGGAGGCGGCAGCGAGGGCGGAGGCAGCGGCGGCGGCCTGAACGACATC TTCGAGGCCC</u> (60) | 4 |
| AP-4R | GGCAGCGCGGCCGCTTACTCGTGCCACTCGATCTTCT<u>GGGCCTCGAAGAT GTCGTTC</u> (57) | 5 |
| AP-PvuI-SalI-3F | <u>GCGGAGGCGGCAGCGAGGGC</u>CGATCGGGTGTCGACGGCCT<u>GAACGACATC TTCGAGGCCC</u> (60) | 6 |
| H8-PvuI-F | CGCACCATCACCACCACCACCATCACCGAT (30) | 7 |
| H8-PvuI-R | CGGTGATGGTGGTGGTGGTGATGGTGCGAT (30) | 8 |
| H8-TagRFP-T-PvuI-F | GGCCGATCGCACCATCACCACCACCACCATCACATGGTGTCTAAGGGCGA AGAG (54) | 9 |
| H8-TagRFP-T-SalI-R | GCCACCGTCGACCTTGTCGTCGTCGTCCTTGTACAGCTCGTCCATGC (47) | 10 |

FIGS. 1a and 1b schematically show the 3-dimensional structure of Nlg-1 dimer, locations of major amino acids, and the constitution of domains of the complex according to the present invention and those of various complexes designed for comparison.

Example 3: Establishment of Stable Cell Lines

To the 1.5 mL of Opti-MEM I Reduced Serum Media was added 24 μs of each Nlg-1-encoding plasmid DNA (pNHY-Nlg-1-AP, pNHR-Nlg-1-AP, and pNH-Nlg-1-R-AP). Likewise, 60 μL of a 1.0 mg/mL PEI solution was added to the 1.5 mL of an Opti-MEM solution. After incubation at 25° C. for 5 minutes, the two solutions were mixed at room cells transfected with the plasmid were cultured for 3 days to 6 days at 37° C. to allow the in vivo biotinylated Nlg-1 to be secreted into the culture medium. Then, 10 mL of the medium was saved and the whole cells were transferred to a culture dish with a diameter of 15 cm and filled with 30 mL of DMEM containing 100 μg/mL G418 and 10 μM biotin. After another three days, the culture medium was combined with the saved medium and subjected to column purification using 2 mL of Ni-NTA resin according to the manufacturer's protocol.

Meanwhile, for in vitro biotinylation, the stable cell line was grown without BirA transfection. Instead, the purified Nlg-1 was treated with BirA enzyme. Specifically, to 1 mL of a column elution fraction showing the highest fluorescence signal was added 5 mM $MgCl_2$, 1 mM ATP, 0.1 mM biotin, and 30 nM BirA enzyme as final concentrations and incubated at 37° C. while shaking for 2 hours. The levels of in vivo and in vitro biotinylation were analyzed via western blot using SAV-HRP or using goat or mouse anti-Nlg-1 antibody and HRP-conjugated secondary antibody. The purity of Nlg-1 was analyzed by SDS-PAGE with silver staining, followed by quantification using NIH ImageJ software. The Nlg-1 concentration obtained from the image analysis was compared to fluorescence intensity measured with a Synergy Mx fluorescence microplate reader (BioTek, Seoul, Korea).

Example 5: Reconstitution of Nlg-1-RFP-AP on Microbeads

Egg PC mixed with Biotin-Cap-PE (L-α-phosphatidylcholine, 99 mol % egg PC and 1 mol % Biotin-Cap-PE) in chloroform was dried, hydrated, and filter-sterilized using PBS (1 mL, 100 mM, pH 7.4) to yield 5 mg/mL initial concentrations of phospholipids. The SUV was generated by extrusion through 50 nm pores and diluted in PBS to a final concentration of 1 mg/mL. The solution (450 μL) was mixed with 1 μL of autoclaved silica microbeads (about $3.0 \times 10^5$ beads) at 25° C. for 30 minutes and incubated while vortexing intermittently. After rinsing twice with 1 mL PBS, the beads were incubated with PBS (1 mL) containing BSA (100 μg/mL) at 25° C. for 45 minutes. The beads were washed with PBS (1 mL), treated with SAV (170 nM for 1% (mol/mol) Biotin-Cap-PE), and incubated at 25° C. for 45 minutes. After rinsing three times with 1 mL PBS, the beads were treated with 1 mL of the biotinylated Nlg-1 solution and incubated overnight at 4° C. For the display of biotinylated Nlg-1 on polymeric microbeads, Dynabeads M-280 stock solution (1 μL, $6 \times 10^5$ to $7.0 \times 10^5$ beads) was added to the Nlg-1 solution (1 mL) and incubated at 25° C. for 3 hours. The thus-prepared Nlg-1 coated beads, SLB beads, and Dynabeads were added to cultured hippocampal neurons (17 DIV) and incubated at 37° C. and 5% $CO_2$ atmosphere for 24 hours.

Example 6: Neuronal Cell Culture

Primary hippocampal neurons were obtained from Sprague-Dawley rat embryos at day 18 of gestation (E18). Specifically, hippocampi dissected from E18 rat embryos were rinsed with HBSS, and then incubated with papain and DNase at 37° C. while stirring at a rate of 60 rpm for 30 minutes. After sequential rinsing with solutions of 10% and 5% FBS in HBSS, individual single cells were mechanically isolated by performing trituration 10 times in 2 mL HBSS containing DNase with a silanized Pasteur pipette (the pipette tip was barely polished with fire). The cell suspension was diluted to a density of $2 \times 10^5$ cells/mL with a plating medium containing MEM supplemented with 0.6% (w/v) glucose, 10 mM sodium pyruvate, 1 mg/mL FBS, and 1% penicillin-streptomycin. Then, the cell-medium solution plated on the PDK-coated glass was placed in a Petri dish. Three hours thereafter, the cell culture medium was exchanged with a B27-supplemented neurobasal medium containing 2 mM glutamax. Cultures were maintained in an incubator at 37° C. and 5% $CO_2$ atmosphere.

Example 7: Immunocytochemistry

Cells were fixed using 4% formaldehyde for 25 minutes and rinsed 3 times with PBS (100 mM, pH 7.4). The cells were then incubated in a blocking solution, containing 4% BSA and 0.1% Triton X-100 dissolved in PBS, for 30 minutes, and incubated in primary antibodies, diluted in Tris-buffered saline (TBS, pH 7.4) containing 0.5% BSA and 0.1% Triton X-100, at 4° C. overnight. The samples were then washed three times with TBS and the fluorescent secondary antibodies were applied in TBS containing 0.5% BSA solution at room temperature for 1 hour. The samples were washed again three times with TBS and once with DDW, and stored in VECTASHIED Mounting Medium containing DAPI at −80° C. until microscopic examination. Fluorescence images were taken with a Zeiss LSM710 confocal laser scanning microscope equipped with ZEN 2009 software at the National Center for Inter-university Research Facilities (NCIRF) of Seoul National University (Korea).

Example 8: Image Quantification and Analysis

Fluorescence quantification was performed using NIH ImageJ software. Fluorescence intensities were measured from at least 10 beads under the same experimental conditions and the data from at least three separate immunostaining experiments was averaged. A fluorescence ratio was determined by measuring the intensity of each channel of the same region of interest (ROI) that includes augmented signals around the beads.

Experimental Example 1: Preparation and Purification of Proteins

The present inventors attempted to confirm the functional interactions between the complex including a fluorescent protein, biotin, and Nlg-1 and cultured hippocampal neurons, independent of SLB media. The fluorescence tag can aid in establishing stable cell lines, and thus mass production, quantification, and tracking of Nlg-1 on a given artificial substrate. Nlg-1 conjugated to the glycosylphosphatidylinositol (GPI)-anchoring motif is known to maintain its activity both in vivo and in vitro. As such, a complex in which a GPI-anchoring motif was conjugated at its C-terminus was prepared and used as a comparative example.

In the present invention, to facilitate protein purification, soluble and secreted forms of Nlg-1 were used. Although the Nlg-1-GPI contains Leu48-Pro631 of extracellular globular region, the crystal structure of Nlg-1/Nrx-1β complex revealed that Leu636, as the end of the α-helix, was required for Nlg-1 dimerization (FIG. 1a). Additionally, Nlg-1-638 was the minimum domain functionally secreted to a culture medium, whereas Nlg-1-626 and Nlg-1-633 were not. Since the GPI motif linked to Nlg-1-631 begins with a KLLSATA amino acid sequence that has a high α-helical propensity, the overall Nlg-1-GPI structure may have remained unaltered. Accordingly, the present inventors retained Nlg-1-639, which includes the minimum domain functionally secreted, and replaced O-glycosylation-rich domain (OG)-transmembrane domain (TMD)-cytoplasmic domain (CD) domains with glycine-serine (GS) linker and a biotin acceptor peptide (AP) tag to maintain the functional structure of Nlg-1 (FIG. 1b). The AP-tagged Nlg-1 was biotinylated in vivo by transient transfection of the Nlg-1 expressing stable cell lines with endoplasmic reticulum (ER)-specific BirA plasmid (FIG. 2). The quantification of the thus-prepared proteins was quantified using analytical methods such as electrophoresis and western blot, based on the BSA prepared at a known concentration (FIG. 3).

Experimental Example 2: Reconstitution of a Complex on a Substrate, and Effects According to the Kinds of Fluorescent Proteins within a Complex and their Positions A biotinylated Nlg-1 complex including a fluorescent protein according to the present invention was conjugated on a substrate. As the substrate, silica microbeads coated with phospholipids containing a lipid biotin tag (BTN-SLB Beads) and streptavidin-coated Dynabeads (Dynabeads SAV) without a lipid bilayer were used. The lipid membrane was used so that the biotin-tagged lipid was contained in an amount of 1%, and in particular, about $9 \times 10^5$ complexes were conjugated per bead with a diameter of 5 The amount of the complexes conjugated to each bead can be increased or reduced by adjusting the ratio of biotin-tagged lipid within the total phospholipids. For example, the present inventors have confirmed that a stronger fluorescent signal appeared when the complex was conjugated to the beads containing the biotin-tagged lipid in an amount of 10%. This result is contrasted by the previous report that 80 to 480 Nlg-1-GPI proteins per 5 μm diameter silica bead are required for neuronal activation, and from the fact that a higher number of complexes can be conjugated per unit bead, it was confirmed that the lifetime of the artificial synapse inducers conjugated to substrates for neuronal activation can be extended. In the case of Dynabeads on which the number of active sites of SAV molecules was optimized, the fluorescence signal was stronger than that of the SLB-silica beads (FIG. 4, left vs. right), and in particular, the binding affinities were confirmed by comparing the fluorescence intensity of fluorescent proteins by respectively conjugating the complexes, which were prepared by varying the kinds of the fluorescent proteins and the positions of the fluorescent proteins and Nlg-1, to BTN-SLB beads and Dynabeads SAV. As a result, as shown in FIG. 3, the fluorescence intensity was increased more in the complex containing YFP as a fluorescent protein than in the complex containing RFP as a fluorescent protein (FIG. 4, YN vs. RN). In particular, it was confirmed that when the fluorescent protein was conjugated at the C-terminus of Nlg-1 in the sequence of Nlg-1-RFP-biotin from the N-terminus, the fluorescence intensity was significantly increased (FIG. 4, RN vs. NR). This can be explained by the fact that YFP itself can be dimerized to thereby inhibit the dimerization of Nlg-1, and that YFP can be more easily photobleached than RFP.

Additionally, the effect of the kinds of fluorescent proteins on the Nlg-1 activity was confirmed. Although N-terminally YFP-tagged Nlg-1 was proven to have a functional role in synaptogenesis, in vivo biotinylated YFP-Nlg-1-AP was rarely functional on both SLB membrane beads and on commercially available Dynabeads M-280 coated with an optimum amount of SAV (FIGS. 5a and 5b). In the present invention, in order to avoid potential hindrance originating from YFP dimerization and photobleaching, YFP was replaced with TagRFP-T16, a photostable monomeric RFP, to thereby yield Nlg-1 with improved activity (FIGS. 5c and 5d). Consequently, only the Nlg-1-RFP-AP complex, in which Nlg-1 was conjugated to the N-terminal direction of TagRFP-T, was able to induce presynaptic differentiation, recruiting synapsin I and vesicular glutamate transporter 1, which are presynaptic marker proteins (VGlut1) (FIGS. 6a and 6b).

Experimental Example 3: Selective Induction of an Excitatory Presynaptic Differentiation Presynaptic differentiation has been conventionally induced by polybasic materials, such as poly-D-lysine (PDK) and phosphatidylethanolamine (PE). In this regard, the present inventors used PDK microbeads as comparative example. They confirmed that presynaptic differentiation can be induced in neurites in contact with PDK microbeads by introducing both synapsin I and VGlut1, as previously reported (FIG. 6c). However, the expression levels of aggregated presynaptic markers were different from each other. Specifically, synapsin I, a synaptic marker, gathered around the beads of both PDK and Nlg1-RFP-AP beads with similar intensities (FIGS. 6a to 6c and FIGS. 5 to 10). In contrast, the aggregation level of VGlut1, a representative excitatory presynaptic marker, was significantly low in the case of PDK beads compared to Nlg-1-RFP-AP beads (FIG. 6d). Additionally, the neurite-contacting Nlg-1-RFP-AP beads showed a significantly higher rate of synapsin I aggregation than the neurite-contacting PDK beads (FIG. 9). These results suggest that Nlg-1-RFP-AP is a more potent inducer for excitatory glutamatergic synapses than PDK for cultured hippocampal neurons.

Meanwhile, synapsin I is widely used as a general synaptic marker, but its distribution in neurons is quite delocalized such that the synapsin I puncta are frequently observed in the absence of synapses. Therefore, it is necessary to confirm the relationship between synapsin I puncta and synapses using other presynaptic markers. The present inventors confirmed, in addition to synapsin I and VGlut1, the expression of Bassoon protein capable of labeling the presynaptic active zone, which is the site for secretion of neurotransmitters and is the nearest site directly paralleled with the postsynaptic density (PSD). In the hippocampal neurons, cytomatrix protein Bassoon and the synaptic vesicle protein synapsin I showed different distribution profiles. Bassoon mainly resides within about 70 nm from the synaptic cleft, whereas synapsin I populates within the region of about 70 nm to 200 nm distant from the synaptic cleft. In the present invention, given the diffraction resolution limit of confocal microscopy is about 200 nm to about 250 nm, it was confirmed that the enhanced synapsin I puncta were always accompanied by and were distinguished from the enhanced Bassoon puncta, with Bassoon being closer to the beads (FIGS. 7a to 7c, and FIG. 11). Additionally, the neurite-contacting Nlg-1-RFP-AP beads showed a significantly higher rate of Bassoon aggregation than the neurite-contacting PDK beads (FIG. 11).

Additionally, the present inventors confirmed the specificity of Nlg-1-RFP-AP to excitatory presynaptic differentiation by comparing with the expression of glutamic acid decarboxylase (GAD), a presynaptic marker protein for the inhibitory GABA synapses. Not only the Nlg-1-RFP-AP complex on the SLB beads but also that on the non-SLB beads showed higher preference for the excitatory presynaptic marker, VGlut1, but not for GAD (FIGS. 8a to 8d, and FIG. 12). The GAD, in general, showed discrete strong background signals with random distribution and in an all-or-none fashion, yielding stochastic colocalization with VGlut1, which were ruled out in fluorescence intensity calculations (FIG. 12c, arrow). As in FIG. 6c, the PDK beads induced an increase in the expression level of VGlut1, but there was also an increase of GAD population around the PDK beads, as previously reported (FIGS. 8c and 8d). Additionally, there were occasional GAD-positive only puncta (FIG. 12d, arrow) as well as VGlut1- and GAD-positive puncta (FIG. 12d, arrowhead). Overall, the PDK beads gave bead-shaped GAD-positive puncta, whereas the Nlg-1 beads did not.

Lastly, the present inventors confirmed that the signals of synaptic markers increased as the fluorescence intensity from the Nlg-1-RFP-AP, which was conjugated to a substrate, increased, i.e., as the number of the complexes increased, regardless of the kinds of the substrate. This indicates that the activity of Nlg-1-RFP-AP is irrelevant to the method of immobilizing it to a substrate, and it simply relies on the degree of conjugation.

The mechanism of inducing an excitatory presynaptic differentiation by a complex, according to the present invention, containing a polypeptide, which includes an extracellular domain of Nlg-1, RFP, and biotin tagged at the C-terminus in this order is shown in FIG. 13. Additionally, the principle of inhibition of presynaptic differentiation in a complex containing RFP in the N-terminus is also illustrated therein along with a non-specific differentiation mechanism by a polybasic substrate such as PDK.

Experimental Example 4: Difference between synapses induced by Nlg-1 and PDK In order to confirm the difference between the synapses induced by Nlg-1, a synaptogenic protein, according to the present invention, and the synapses induced by PDK, a polybasic material which has been conventionally used for induction of presynaptic differentiation, the beads coated with Nlg-1 beads and PDK, respectively, i.e., Nlg-1 beads and PDK beads, were cultured after addition thereof to neurons, and the induced synapses were compared by immunochemical fluorescence analysis. In order to confirm the difference according to culture period and contacting hours, experiments were performed by adding beads at different points of culture. The cells isolated in Example 6 were used as the neurons, and the neurobasal medium described in Example 6 was used and cultured. The result of the immunochemical fluorescence analysis is shown in FIG. 14.

As shown in FIG. 14, when the cells were cultured with the beads, the PDK was recognized as a simple adhesion protein, and thus the induction of a synapse failed (FIG. 14a). This is also supported in the literature by Dr. Colman (A. L. Lucido et al., 2009, 29(40):12449-12466). Meanwhile, it was confirmed that the Nlg-1 beads induced a concrete formation of synapses if in contact with cells regardless of the developmental stage of the cells added thereto (0 DIV to 17 DIV) (FIGS. 14a to 14e).

Additionally, the synapses formed by the Nlg-1 beads were firmly maintained as the culture hours increased, whereas the synapses formed by PDK were either weakened or lost without long-term maintenance (FIGS. 14a to 14e).

From the above results, the synapses formed by Nlg-1, a synaptogenic protein, according to the present invention, were shown to have characteristics different from those of the synapses formed by PDK, a polybasic material. Accordingly, considering that the formation of synapses which are firm and can be maintained long-term are required for the establishment of a new neural network through artificial synapses, an artificial synapse inducer including a synaptogenic protein such as Nlg-1, which can form a synapse by contacting with neural cells regardless of the developmental stage of the cells and maintain the formed synapse long-term, is preferable for the purpose of forming a neural interface capable of simulating the real brain environment.

The invention claimed is:

1. An artificial synapse inducer comprising:
a complex comprising a polypeptide and a biotin conjugated to the polypeptide, wherein the polypeptide comprises the sequence of SEQ ID NO: 11; and
a substrate coated with a biotin-binding protein,
wherein the biotin and the biotin-binding protein are bound together such that the complex is attached to the substrate without a lipid bilayer.

2. The artificial synapse inducer of claim 1, wherein the biotin-binding protein is selected from the group of avidin-like proteins consisting of streptavidin, traptavidin, and neutravidin.

3. The artificial synapse inducer of claim 1, wherein the substrate comprises a microbead.

4. The artificial synapse inducer of claim 1, the complex comprises a fluorescent protein.

5. The artificial synapse inducer of claim 4, wherein the fluorescent protein is selected from the group consisting of red fluorescent protein (RFP), blue fluorescent protein (BFP), green fluorescent protein (GFP) and yellow fluorescent protein (YFP).

6. The artificial synapse inducer of claim 1, wherein the complex further comprises a polyhistidine-tag (His-tag) or influenza hemagglutinin epitope tag (HA-tag).

7. The artificial synapse inducer of claim 1, wherein the biotin is conjugated to the polypeptide via a linking peptide connected to Isoleucine located at the C-terminus of SEQ ID NO: 11.

8. The artificial synapse inducer of claim 7, wherein the linking peptide comprises a glycine-serine linker (GS) and a biotin acceptor peptide (AP).

9. A method of forming the artificial synapse inducer of claim 1, the method comprising:
providing a substrate coated with a biotin-binding peptide;
providing a complex comprising a polypeptide and a biotin conjugated to the polypeptide, wherein the polypeptide comprises the sequence of SEQ ID NO: 11; and
applying the complex onto the substrate for causing the biotin and the biotin-binding peptide to bind together such that the complex is attached to the substrate without a lipid bilayer, thereby forming the artificial synapse inducer.

10. The method of claim 9, wherein the biotin is conjugated to the polypeptide via a linking peptide connected to Isoleucine located at the C-terminus of SEQ ID NO: 11.

11. The method of claim 10, the linking peptide comprises a glycine-serine linker (GS) and a biotin acceptor peptide (AP).

12. The method of claim 9, wherein the artificial synapse inducer further comprises a fluorescent protein introduced into the complex.

13. The method of claim 9, wherein the fluorescent protein comprises red fluorescent protein (RFP), blue fluorescent protein (BFP), green fluorescent protein (GFP) and yellow fluorescent protein (YFP).

14. The method of claim 9, wherein the complex further comprises a polyhistidine-tag (His-tag) or influenza hemagglutinin epitope tag (HA-tag).

* * * * *

SEQUENCE LISTING

<160> NUMBER OF SEQ ID NOS: 11

<210> SEQ ID NO 1
<211> LENGTH: 592
<212> TYPE: PRT
<213> ORGANISM: Rattus norvegicus

<400> SEQUENCE: 1

```
Leu Asp Asp Val Asp Pro Leu Val Thr Thr Asn Phe Gly Lys Ile Arg
1               5                   10                  15

Gly Ile Lys Lys Glu Leu Asn Asn Glu Ile Leu Gly Pro Val Ile Gln
            20                  25                  30

Phe Leu Gly Val Pro Tyr Ala Ala Pro Pro Thr Gly Glu His Arg Phe
        35                  40                  45

Gln Pro Pro Glu Pro Pro Ser Pro Trp Ser Asp Ile Arg Asn Ala Thr
    50                  55                  60

Gln Phe Ala Pro Val Cys Pro Gln Asn Ile Ile Asp Gly Arg Leu Pro
65                  70                  75                  80

Glu Val Met Leu Pro Val Trp Phe Thr Asn Asn Leu Asp Val Val Ser
                85                  90                  95

Ser Tyr Val Gln Asp Gln Ser Glu Asp Cys Leu Tyr Leu Asn Ile Tyr
            100                 105                 110

Val Pro Thr Glu Asp Val Lys Arg Ile Ser Lys Glu Cys Ala Arg Lys
        115                 120                 125

Pro Gly Lys Lys Ile Cys Arg Lys Gly Asp Ile Arg Asp Ser Gly Gly
    130                 135                 140

Pro Lys Pro Val Met Val Tyr Ile His Gly Gly Ser Tyr Met Glu Gly
145                 150                 155                 160

Thr Gly Asn Leu Tyr Asp Gly Ser Val Leu Ala Ser Tyr Gly Asn Val
                165                 170                 175
```

```
Ile Val Ile Thr Val Asn Tyr Arg Leu Gly Val Leu Gly Phe Leu Ser
            180                 185                 190

Thr Gly Asp Gln Ala Ala Lys Gly Asn Tyr Gly Leu Leu Asp Leu Ile
        195                 200                 205

Gln Ala Leu Arg Trp Thr Ser Glu Asn Ile Gly Phe Phe Gly Gly Asp
    210                 215                 220

Pro Leu Arg Ile Thr Val Phe Gly Ser Gly Ala Gly Gly Ser Cys Val
225                 230                 235                 240

Asn Leu Leu Thr Leu Ser His Tyr Ser Glu Gly Asn Arg Trp Ser Asn
                245                 250                 255

Ser Thr Lys Gly Leu Phe Gln Arg Ala Ile Ala Gln Ser Gly Thr Ala
            260                 265                 270

Leu Ser Ser Trp Ala Val Ser Phe Gln Pro Ala Lys Tyr Ala Arg Ile
        275                 280                 285

Leu Ala Thr Lys Val Gly Cys Asn Val Ser Asp Thr Val Glu Leu Val
    290                 295                 300

Glu Cys Leu Gln Lys Lys Pro Tyr Lys Glu Leu Val Asp Gln Asp Val
305                 310                 315                 320

Gln Pro Ala Arg Tyr His Ile Ala Phe Gly Pro Val Ile Asp Gly Asp
                325                 330                 335

Val Ile Pro Asp Asp Pro Gln Ile Leu Met Glu Gln Gly Glu Phe Leu
            340                 345                 350

Asn Tyr Asp Ile Met Leu Gly Val Asn Gln Gly Glu Gly Leu Lys Phe
        355                 360                 365

Val Glu Asn Ile Val Asp Ser Asp Asp Gly Val Ser Ala Ser Asp Phe
    370                 375                 380

Asp Phe Ala Val Ser Asn Phe Val Asp Asn Leu Tyr Gly Tyr Pro Glu
385                 390                 395                 400

Gly Lys Asp Val Leu Arg Glu Thr Ile Lys Phe Met Tyr Thr Asp Trp
                405                 410                 415

Ala Asp Arg His Asn Pro Glu Thr Arg Arg Lys Thr Leu Leu Ala Leu
            420                 425                 430

Phe Thr Asp His Gln Trp Val Ala Pro Ala Val Ala Thr Ala Asp Leu
        435                 440                 445

His Ser Asn Phe Gly Ser Pro Thr Tyr Phe Tyr Ala Phe Tyr His His
    450                 455                 460

Cys Gln Thr Asp Gln Val Pro Ala Trp Ala Asp Ala Ala His Gly Asp
465                 470                 475                 480

Glu Val Pro Tyr Val Leu Gly Ile Pro Met Ile Gly Pro Thr Glu Leu
                485                 490                 495

Phe Pro Cys Asn Phe Ser Lys Asn Asp Val Met Leu Ser Ala Val Val
            500                 505                 510

Met Thr Tyr Trp Thr Asn Phe Ala Lys Thr Gly Asp Pro Asn Gln Pro
        515                 520                 525

Val Pro Gln Asp Thr Lys Phe Ile His Thr Lys Pro Asn Arg Phe Glu
    530                 535                 540

Glu Val Ala Trp Thr Arg Tyr Ser Gln Lys Asp Gln Leu Tyr Leu His
545                 550                 555                 560

Ile Gly Leu Lys Pro Arg Val Lys Glu His Tyr Arg Ala Asn Lys Val
                565                 570                 575

Asn Leu Trp Leu Glu Leu Val Pro His Leu His Asn Leu Asn Asp Ile
            580                 585                 590
```

<210> SEQ ID NO 2
<211> LENGTH: 66
<212> TYPE: DNA
<213> ORGANISM: Artificial Sequence
<220> FEATURE:
<223> OTHER INFORMATION: AP-1F

<400> SEQUENCE: 2
ggcggtggta cctcatctgc ataatctcaa tgacattggc ggcggcagcg gcggaggcag    60
cgaggg                                                               66

<210> SEQ ID NO 3
<211> LENGTH: 60
<212> TYPE: DNA
<213> ORGANISM: Artificial Sequence
<220> FEATURE:
<223> OTHER INFORMATION: AP-2R

<400> SEQUENCE: 3
gccctcgctg ccgcctccgc tgccgcctcc gctgcctccg ccctcgctgc ctccgccgct    60

<210> SEQ ID NO 4
<211> LENGTH: 60
<212> TYPE: DNA
<213> ORGANISM: Artificial Sequence
<220> FEATURE:
<223> OTHER INFORMATION: AP-3F

<400> SEQUENCE: 4
gcggaggcgg cagcgagggc ggaggcagcg gcggcggcct gaacgacatc ttcgaggccc    60

<210> SEQ ID NO 5
<211> LENGTH: 57
<212> TYPE: DNA
<213> ORGANISM: Artificial Sequence
<220> FEATURE:
<223> OTHER INFORMATION: AP-4R

<400> SEQUENCE: 5
ggcagcgcgg ccgcttactc gtgccactcg atcttctggg cctcgaagat gtcgttc      57

<210> SEQ ID NO 6
<211> LENGTH: 60
<212> TYPE: DNA
<213> ORGANISM: Artificial Sequence
<220> FEATURE:
<223> OTHER INFORMATION: AP-PvuI-SalI-3F

<400> SEQUENCE: 6
gcggaggcgg cagcgagggc cgatcgggtg tcgacggcct gaacgacatc ttcgaggccc    60

<210> SEQ ID NO 7
<211> LENGTH: 30
<212> TYPE: DNA
<213> ORGANISM: Artificial Sequence
<220> FEATURE:
<223> OTHER INFORMATION: H8-PvuI-F

<400> SEQUENCE: 7
cgcaccatca ccaccaccac catcaccgat                                     30

<210> SEQ ID NO 8
<211> LENGTH: 30
<212> TYPE: DNA
<213> ORGANISM: Artificial Sequence
<220> FEATURE:
<223> OTHER INFORMATION: H8-PvuI-R

<400> SEQUENCE: 8
cggtgatggt ggtggtggtg atggtgcgat                              30

<210> SEQ ID NO 9
<211> LENGTH: 54
<212> TYPE: DNA
<213> ORGANISM: Artificial Sequence
<220> FEATURE:
<223> OTHER INFORMATION: H8-TagRFP-T-PvuI-F

<400> SEQUENCE: 9
ggccgatcgc accatcacca ccaccaccat cacatggtgt ctaagggcga agag    54

<210> SEQ ID NO 10
<211> LENGTH: 47
<212> TYPE: DNA
<213> ORGANISM: Artificial Sequence
<220> FEATURE:
<223> OTHER INFORMATION: H8-TagRFP-T-SalI-R

<400> SEQUENCE: 10
gccaccgtcg accttgtcgt cgtcgtcctt gtacagctcg tccatgc           47

<210> SEQ ID NO 11
<211> LENGTH: 213
<212> TYPE: PRT
<213> ORGANISM: Artificial sequence
<220> FEATURE:
<223> OTHER INFORMATION: Peptide

<400> SEQUENCE: 11

Ser Ala Ser Asp Phe Asp Phe Ala Val Ser Asn Phe Val Asp Asn Leu
1               5                   10                  15

Tyr Gly Tyr Pro Glu Gly Lys Asp Val Leu Arg Glu Thr Ile Lys Phe
                20                  25                  30

Met Tyr Thr Asp Trp Ala Asp Arg His Asn Pro Glu Thr Arg Arg Lys
            35                  40                  45

Thr Leu Leu Ala Leu Phe Thr Asp His Gln Trp Val Ala Pro Ala Val
    50                  55                  60

Ala Thr Ala Asp Leu His Ser Asn Phe Gly Ser Pro Thr Tyr Phe Tyr
65                  70                  75                  80

Ala Phe Tyr His His Cys Gln Thr Asp Gln Val Pro Ala Trp Ala Asp
                85                  90                  95

Ala Ala His Gly Asp Glu Val Pro Tyr Val Leu Gly Ile Pro Met Ile
            100                 105                 110

Gly Pro Thr Glu Leu Phe Pro Cys Asn Phe Ser Lys Asn Asp Val Met
        115                 120                 125

Leu Ser Ala Val Val Met Thr Tyr Trp Thr Asn Phe Ala Lys Thr Gly
    130                 135                 140

Asp Pro Asn Gln Pro Val Pro Gln Asp Thr Lys Phe Ile His Thr Lys
145                 150                 155                 160

Pro Asn Arg Phe Glu Glu Val Ala Trp Thr Arg Tyr Ser Gln Lys Asp
                165                 170                 175

Gln Leu Tyr Leu His Ile Gly Leu Lys Pro Arg Val Lys Glu His Tyr
            180                 185                 190

Arg Ala Asn Lys Val Asn Leu Trp Leu Glu Leu Val Pro His Leu His
        195                 200                 205

Asn Leu Asn Asp Ile
210